(12) United States Patent
Isei et al.

(10) Patent No.: US 8,459,073 B2
(45) Date of Patent: Jun. 11, 2013

(54) METHOD FOR MEASURING SHEET MATERIAL FLATNESS AND METHOD FOR PRODUCING STEEL SHEET USING SAID MEASURING METHOD

(75) Inventors: Yoshito Isei, Osaka (JP); Tomoya Kato, Osaka (JP); Masahiro Osugi, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/444,342

(22) Filed: Apr. 11, 2012

(65) Prior Publication Data

US 2012/0204614 A1    Aug. 16, 2012

Related U.S. Application Data

(63) Continuation of application No. PCT/JP2010/063068, filed on Aug. 3, 2010.

(30) Foreign Application Priority Data

Oct. 19, 2009   (JP) .................................. 2009-240574

(51) Int. Cl.
*B21B 37/00* (2006.01)
*B21C 51/00* (2006.01)

(52) U.S. Cl.
USPC ..................... 72/9.2; 72/11.2; 72/11.8; 72/37

(58) Field of Classification Search
USPC .............. 72/7.1–14.8, 201, 37; 348/135, 136, 348/143, 148, 149, 152; 250/559.05, 559.07, 250/559.08; 700/154
See application file for complete search history.

(56) References Cited

U.S. PATENT DOCUMENTS 7,184,585 B2 *   2/2007   Hamza et al. .................. 348/135

FOREIGN PATENT DOCUMENTS

| JP | 61-40503 | 2/1986 |
|----|----------|--------|
| JP | 11-104721 | 4/1999 |
| JP | 2008-58036 | 3/2008 |

* cited by examiner

*Primary Examiner* — Dana Ross
*Assistant Examiner* — Pradeep C Battula
(74) *Attorney, Agent, or Firm* — Clark & Brody

(57) ABSTRACT

A method for measuring flatness of a sheet material in which a light and dark pattern composed by a light portion and a dark portion is projected onto a surface of the sheet material running in a longitudinal direction, a pattern image is acquired by photographing the light and dark pattern by an image pickup device having an image pickup visual field larger than a width of the sheet material, and the flatness of the sheet material is measured by analyzing the acquired pattern image. A staggered pattern is used for the projecting step and for light to be specularly reflected for receipt by the image pickup device. Calculating the flatness also includes steps of setting a shape measurement line, averaging picture element concentrations, calculating a distribution of the concentrations, and calculating the flatness based on surface shape using the distribution.

6 Claims, 17 Drawing Sheets

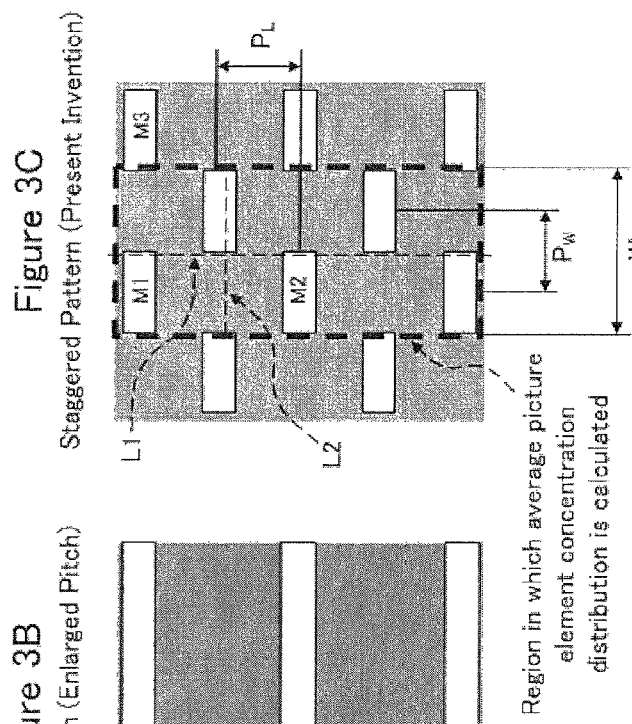
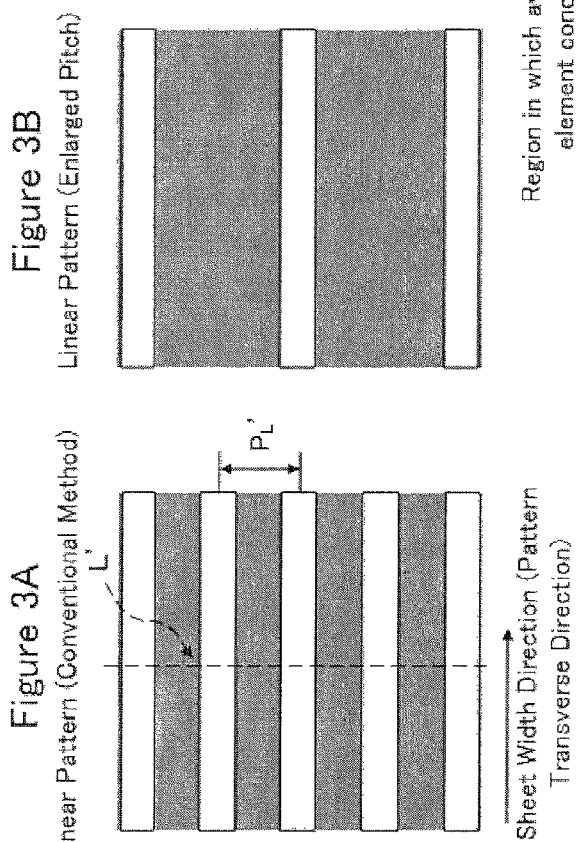
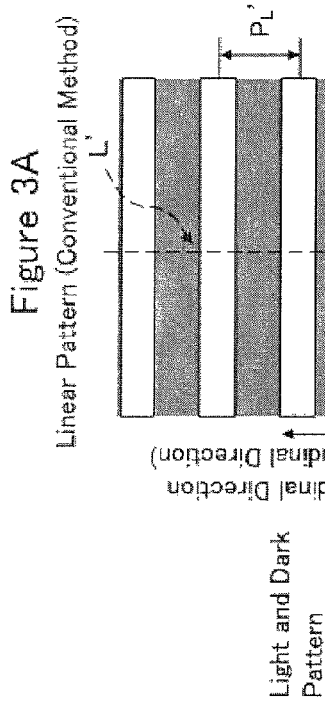

Sheet Longitudinal Direction (Pattern Longitudinal Direction)

Sheet Width Direction (Pattern Transverse Direction)

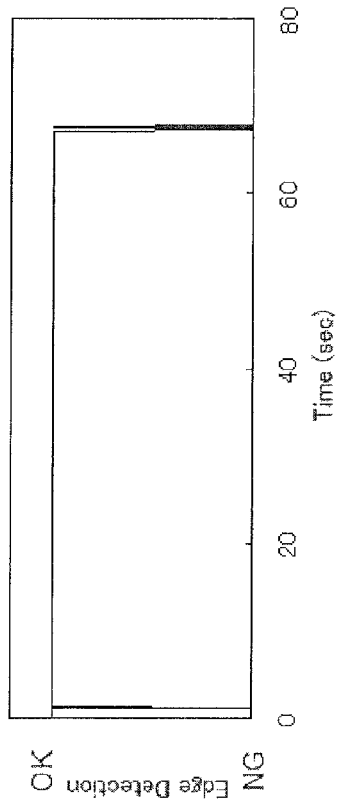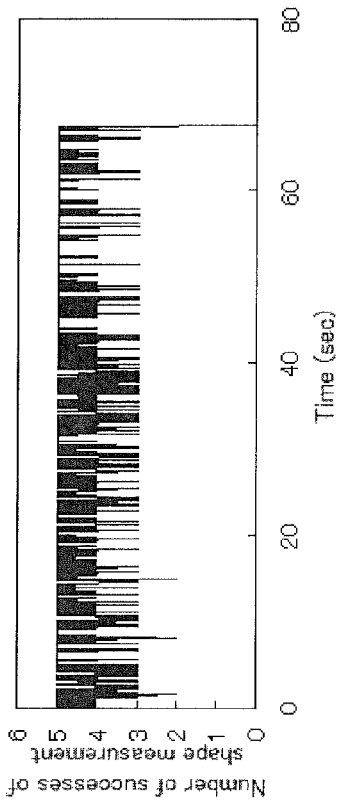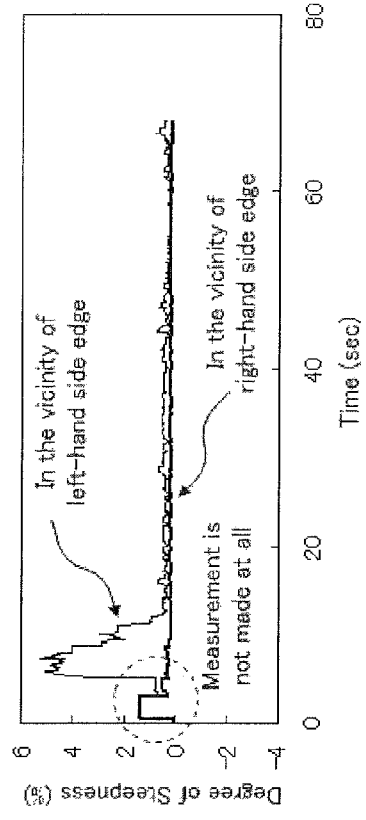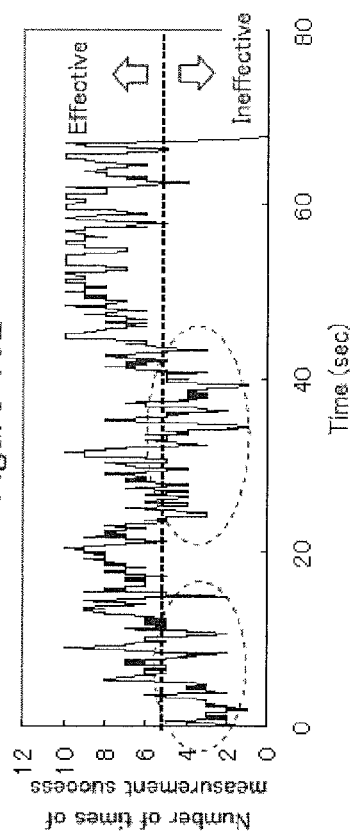

METHOD FOR MEASURING SHEET MATERIAL FLATNESS AND METHOD FOR PRODUCING STEEL SHEET USING SAID MEASURING METHOD

TECHNICAL FIELD

The present invention relates to a method for measuring, with high accuracy, flatness of a sheet material such as a steel sheet running in the longitudinal direction, and a method for producing a steel sheet using said measuring method.

BACKGROUND ART

A sheet material is required to have high flatness for assuring quality and for consistent production. In fulfilling this requirement, how the flatness is to be controlled properly in the production process of sheet material has conventionally been a challenge.

Generally, as an index indicative of flatness, difference in elongation percentage or degree of steepness is used.

The difference in elongation percentage $\Delta\epsilon$ is a difference between an elongation percentage $\epsilon_{CENT}$ in a central portion in the width direction of a sheet material and an elongation percentage $\epsilon_{EDGE}$ in a portion other than the central portion in the width direction of the sheet material (generally, in the vicinity of the edge) as measured in a certain section in the longitudinal direction of the sheet material, and is represented by Formula (2).

$$\Delta\epsilon = \epsilon_{CENT} - \epsilon_{EDGE} \quad (2)$$

Also, the degree of steepness $\lambda$ is defined as $\lambda = \delta/P$ by using the height $\delta$ of standing wave of sheet and the pitch $P$ thereof. In the case where the shape of the standing wave of sheet is approximated as a sinusoidal wave, the well-known relationship represented by Formula (3) exists between the difference in elongation percentage $\Delta\epsilon$ and the degree of steepness $\lambda$ (%).

$$\lambda = \begin{cases} +\frac{2}{\pi}|\Delta\varepsilon|^{1/2} \times 100 & (\text{when } \Delta\varepsilon \geq 0) \\ -\frac{2}{\pi}|\Delta\varepsilon|^{1/2} \times 100 & (\text{when } \Delta\varepsilon < 0) \end{cases} \quad (3)$$

For example, the production line for a hot-rolled steel sheet, which is one example of the sheet material, generally comprises a heating furnace, roughing mill, finishing mill train, cooling zone, and coiling machine. A starting material heated in the heating furnace is rolled by the roughing mill to produce a slab (rough bar) having a thickness of 30 to 60 mm. Next, the slab is rolled by the finishing mill train consisting of six to seven finishing mills to produce a hot-rolled steel sheet having a thickness required by the customer. This hot-rolled steel sheet is cooled by the cooling zone, and is coiled by the coiling machine.

The production of a hot-rolled steel sheet having high flatness is important for ensuring the product quality, for stably passing the steel sheet through the finishing mill and coiling it by using the coiling machine, and also for maintaining high productivity. Poor flatness of a hot-rolled steel sheet is caused by unevenness in the sheet width direction of elongation percentage produced in the finishing mill train and cooling zone. Therefore, as a method for producing a hot-rolled steel sheet having high flatness, there has been proposed a method in which a flatness meter or a sheet thickness profile meter is installed between the finishing mills or on the exit of the finishing mill train, and based on the measured value of the meter, the work roll bender of the finishing mill is feedback controlled, or a method in which the setup condition of the shift position of work roll or the load distribution of finishing mill train is controlled by learning. The above-described controlling method is described, for example, in JP11-104721A. Also, there has been proposed a method in which a flatness meter is installed on the exit of the cooling zone, and based on the measured value thereof, the amount of cooling water of cooling nozzles of the cooling zone is feedback controlled. To carry out the above-described controlling method, a method and a device for measuring the flatness of a hot-rolled steel sheet running at a high speed at a location between the finishing mills, on the exit of the finishing mill train, or on the exit of the cooling zone have been devised and used for actual machines.

As a conventional method for measuring the flatness of a hot-rolled steel sheet, there has been known a method in which a linear pattern consisting of a plurality of light lines extending in the sheet width direction is projected onto the surface of the hot-rolled steel sheet that has been hot rolled and is running, the linear pattern is photographed from the direction different from the linear pattern projecting direction by a two-dimensional camera, and based on distortion of the linear pattern in the picked-up image, the surface shape, and therefore the flatness of the hot-rolled steel sheet is measured. In this method, by projecting the linear pattern over the range of about 1 m in the longitudinal direction (rolling direction) of the hot-rolled steel sheet, the measurement accuracy in the state in which standing waves of sheet observed frequently at a location just close to the exit of the finishing mill exist steadily (at the fixed end because the standing waves of sheet are fixed by the finishing mill) is restrained from being deteriorated. The above-described flatness measuring method is described, for example, in JP61-40503A and JP2008-58036A.

JP61-40503A describes a method in which by scanning three laser beams, which are fired spacedly in the longitudinal direction of sheet, at a high speed in the sheet width direction, a linear pattern consisting of three light lines is projected onto the sheet surface, this linear pattern is photographed by a camera, and based on the distortion of the linear pattern in the picked-up image thus obtained, the surface shape, and therefore the flatness of the sheet is measured. However, the linear pattern consisting of three light lines does not allow highly accurate measurement of the sheet surface shape, so that there arises a problem that the measurement accuracy is extremely deteriorated especially when the period of standing waves of sheet is short.

JP2008-58036A describes a method in which a high-density linear pattern consisting of a plurality of light lines extending in the sheet width direction is projected onto the sheet material surface by using a slide on which the high-density linear pattern is drawn, this linear pattern is photographed by a camera, and based on the distortion of the linear pattern in the picked-up image thus obtained, the surface shape, and therefore the flatness of the sheet material is measured. In this method, unlike the method described in JP61-40503A, projection of the high-density linear pattern increases the measurement resolution (space resolution) of the surface shape, so that it can be expected that the surface shape of the sheet material can be measured with high accuracy.

The shape measuring method as described in JP2008-58036A is generally called a grating pattern projection method, and is used widely in various applications, being not limited to the case where the surface shape of a steel sheet is measured.

FIG. 1 is a schematic view showing a configuration example of a device for carrying out the grating pattern projection method. As shown in FIG. 1, in the grating pattern projection method, a grating pattern is projected onto the sheet material surface from the slantwise upper side with respect to the sheet material surface by a projector provided with a light source, a slide on which the grating pattern (generally, a linear pattern) is drawn, and an imaging lens. Then, the grating pattern projected onto the sheet material surface is photographed from the direction different from the grating pattern projecting direction by a two-dimensional camera. At this time, if the surface shape of the sheet material changes, an inclination angle of the sheet material surface also changes, and the pitch of the grating pattern in the picked-up image photographed by the camera (generally, the space between the light lines composing the linear pattern) changes according to the inclination angle of the sheet material surface. The relationship between the inclination angle of the sheet material surface and the pitch of the grating pattern in the picked-up image can be determined geometrically. Therefore, if the pitch of the grating pattern in the picked-up image is measured, the inclination angle of the sheet material surface can be calculated based on this measurement result and the above-described relationship. If the calculated inclination angle is integrated, the surface shape of the sheet material can be calculated.

SUMMARY OF INVENTION

In the case where the surface shape, and therefore the flatness of a hot-rolled steel sheet is measured by using the grating pattern projection method, as described above, a linear pattern consisting of a plurality of light lines extending in the sheet width direction is projected onto the steel sheet surface as the grating pattern. Then, a shape measurement line extending along the longitudinal direction of the hot-rolled steel sheet is set at a position at which the surface shape must be measured to calculate the flatness in the picked-up image of the linear pattern, and based on the picture element concentration distribution on the shape measurement line, the distribution of the pitches in the linear pattern on the shape measurement line (the space between the light lines composing the linear pattern) is calculated. Next, based on the distribution of the pitches in the linear pattern on the shape measurement line, the distribution of inclination angles of the steel sheet surface on the shape measurement line is calculated, and by integrating this inclination angle along the shape measurement line, the surface shape of the steel sheet on the shape measurement line is calculated. Further, based on the calculated surface shape, the flatness is computed.

In the case where a device for carrying out the grating pattern projection method as shown in FIG. 1 is installed on the production line for a hot-rolled steel sheet, and the finishing mill is controlled by feeding back the measured flatness value in real time, the device must be installed at a location just close to the exit of the finishing mill. At the location just close to the exit of the finishing mill, a sufficient installation space for the device cannot be secured in many cases because measuring instruments such as a sheet thickness meter, a sheet width meter, and a sheet thermometer are installed, and besides the cooling zone for water cooling is installed just close to this location.

In order to reduce the installation space for the device as far as possible, it is thought that, firstly, the projector and the camera are brought closer to the hot-rolled steel sheet to reduce the installation space in the vertical direction, and secondly, the angles of view of the projector and the camera are set so as to be on the wide side so that the measurement range (about 1 m in the longitudinal direction) of the hot-rolled steel sheet enters within the angle of view of projection of the projector and within the angle of view of the camera. However, as shown in FIG. 2, in the case where the angle of view of projection of the projector is wide, in order to reduce the installation space in the horizontal direction, the camera must be arranged at a position at which the specularly reflected light of projected light of the projector (the specularly reflected light of linear pattern) can be received. From the viewpoint of enhancing the measurement resolution (space resolution) of the surface shape, a linear pattern having a small pitch has only to be projected. However, since the surface of the hot-rolled steel sheet immediately after being finish rolled has a strong specular reflection property (the reflection intensity of specular reflection component is high), if the camera is arranged at a position at which the specularly reflected light of projected light of the projector can be received, the output signal sent from an element receiving the specularly reflected light of the light receiving elements of the camera saturates, and halation occurs. Therefore, in the picture element region of photographed images corresponding to the element receiving the specularly reflected light and the peripheral elements, the adjacent light lines stick to each other, and the linear pattern is liable to collapse. Also, if the sensitivity of the camera is reduced excessively to prevent the linear pattern from collapsing, the output signal intensity of elements other than the element receiving the specularly reflected light becomes insufficient, so that the concentration of picture element corresponding to the element having an insufficient output signal intensity in the photographed image decreases, and therefore a linear pattern in which the light lines are difficult to distinguish is formed.

The present invention has been made to solve the problems with the prior arts explained above, and accordingly an objective thereof is to provide a method for measuring the flatness of a sheet material such as a steel sheet running in the longitudinal direction, in which even in the case where an image pickup device is arranged at a position at which the specularly reflected light of a light and dark pattern projected onto the surface of a sheet material having a strong specular reflection property can be received, the surface shape of the sheet material can be measured with high accuracy, whereby the flatness of the sheet material can be measured with high accuracy.

In the case where the light and dark pattern projected onto the surface of a sheet material is made the linear pattern having a small pitch, if the image pickup device is arranged at a position at which the specularly reflected light can be received, as the countermeasures for preventing the collapse of the linear pattern in the picture element region corresponding to the element receiving the specularly reflected light and the peripheral elements, the methods described below are conceivable: (1) a method in which a camera having a wide dynamic range is employed as the image pickup device so that even if the sensitivity of the image pickup device is reduced, the output signal intensity of the element that does not receive the specularly reflected light does not become insufficient, and (2) a method in which the pitch of the linear pattern is increased.

However, although a dynamic range of 12 bits (4096 gradation) or larger can be obtained by a digital camera that has come into wide use recently, the countermeasure of item (1) has a problem of restricted wiring length and increased camera cost, and therefore cannot be applied easily in some case.

Also, in the countermeasure of item (2), if the pitch of the linear pattern is increased simply as shown in FIG. 3B, the measurement resolution (space resolution) of the surface shape decreases, which leads to deterioration in the measurement accuracy of the surface shape, and therefore the measurement accuracy of the flatness.

Accordingly, the present inventors conducted studies earnestly, and hit upon an idea that a staggered pattern shown in FIG. 3C is to be used as the light and dark pattern projected onto the surface of the sheet material, the staggered pattern being composed of light portions arranged in a staggered form at a predetermined preset pitch (preset pitch $P_L$ in the longitudinal direction, preset pitch $P_W$ in the transverse direction) in the longitudinal direction and the transverse direction, and this pattern is to be projected onto the surface of the sheet material so that the longitudinal direction of the staggered pattern corresponds to the longitudinal direction of the sheet material, and the transverse direction thereof corresponds to the width direction of the sheet material. With this staggered pattern, since the light portions are arranged in a staggered form in the longitudinal direction and the transverse direction, even if the longitudinal preset pitch $P_L$ between light portions is equal to the preset pitch $P_L'$ of the conventional linear pattern (FIG. 3A), the distance between the light portions adjacent in the longitudinal direction (for example, light portions M1 and M2) becomes longer (or doubled) than the distance $P_L'$ between the light portions adjacent in the longitudinal direction in the conventional linear pattern, and therefore the space between the light portions increases. Concerning the transverse direction, the light portion is continuous in the conventional linear pattern, whereas in the staggered pattern, the light portions adjacent in the straight-line form in the transverse direction (for example, light portions M1 and M3) have a space therebetween. Therefore, the staggered pattern has an advantage that even in the picture element region corresponding to the element or the like of image pickup device receiving the specularly reflected light, the light and dark pattern is difficult to collapse.

However, even if the staggered pattern is used as the light and dark pattern projected onto the surface of the sheet material, if the surface shape of the sheet material is calculated simply based on the distribution of concentrations of picture elements on a shape measurement line L1 extending along the longitudinal direction of the sheet material (the longitudinal direction of the staggered pattern) as in the conventional example, the space between the light portions adjacent in the straight-line form in the longitudinal direction is wide, so that the measurement resolution (space resolution) of the surface shape decreases.

Accordingly, the present inventors further conducted studies earnestly, and hit upon an idea that the concentrations of picture elements on a straight line L2 that extends in the transverse direction of the staggered pattern passing through the picture element on the shape measurement line L1 and has a length W two times or more the transverse preset pitch $P_W$ between the light portions are to be averaged, and thereby an average picture element concentration is to be calculated. For example, it is assumed that the picture element concentration of all light portions of the staggered pattern is 254, and the picture element concentration of all dark portions thereof is zero. Assuming that the length W of the straight line L2 is two times the transverse preset pitch $P_W$ between the light portions ($W=2P_W$), and the number of picture elements of the light portion on the straight line L2 is equal to the number of picture elements of the dark portion, the average picture element concentration on the straight line L2 is 127. If the distribution of average picture element concentrations along the shape measurement line L1 is calculated (the longitudinal position of the straight line L2 is changed), this distribution of average picture element concentrations is a distribution in which the average picture element concentration at the position at which the straight line L2 passes through the light portion is 127, and the average picture element concentration at the position at which the straight line L2 passes through the dark portion only is zero, that is, a distribution having a period that is the same as the longitudinal preset pitch $P_L$ between light portions. In other words, the period $P_L$ of the distribution of the average picture element concentrations is equal to the period $P_L'$ of the distribution of the picture element concentrations on the shape measurement line L' for the conventional linear pattern (FIG. 3A). Therefore, if the surface shape of the sheet material is calculated based on the distribution of the average picture element concentrations, a measurement resolution of the same degree as the case where the conventional linear pattern is used can be obtained without a decrease in measurement resolution (space resolution) of the surface shape for the longitudinal direction of the staggered pattern (the longitudinal direction of the sheet material). The amplitude of distribution of the average picture element concentrations in the case where the staggered pattern is used decreases as compared with the amplitude of distribution of the picture element concentrations in the case where the linear pattern is used. However, if the length W of the straight line L2 on which averaging is performed is made a length two times or more the transverse preset pitch $P_W$ between light portions, the light portion always exists on the straight line L2. Therefore, the amplitude of distribution of the average picture element concentrations is about one-half the case where the linear pattern is used even if decreasing most, which does not pose a problem. Also, the measurement resolution (space resolution) of the surface shape in the transverse direction of the staggered pattern (the width direction of the sheet material) does not pose a problem unless the length W of the straight line L2 is increased extremely because the shape of the hot-rolled steel sheet, which is a main object to which the present invention is applied, does not change suddenly in the width direction although the measurement resolution decreases according to the length W.

As explained above, the present inventors reached a conclusion that if the surface shape of the sheet material is calculated by the procedures of items (A) to (C) described below, even in the case where the image pickup device is disposed at a position at which the specularly reflected light of the light and dark pattern projected onto the surface can be received, the light and dark pattern is difficult to collapse, and the surface shape, and therefore the flatness of the sheet material can be measured with high accuracy without a decrease in measurement resolution.

(A) As the light and dark pattern projected onto the surface of the sheet material, the staggered pattern in which the light portions are arranged in a staggered form at the predetermined preset pitch in the longitudinal direction and the transverse direction is used, and the staggered pattern is projected onto the surface of the sheet material so that the longitudinal direction of the staggered pattern corresponds to the longitudinal direction of the sheet material and the transverse direction thereof corresponds to the width direction of the sheet material.

(B) The concentrations of picture elements on the straight line that extends in the transverse direction of the staggered pattern (the width direction of the sheet material) passing through the picture element on the shape measurement line extending along the longitudinal direction of the staggered pattern (the longitudinal direction of the sheet material) and has a length two times or more the transverse preset pitch $P_W$ between the light portions are averaged, and thereby the average picture element concentration is calculated.

(C) The distribution of the average picture element concentrations along the shape measurement line is calculated, and based on this distribution of the average picture element concentrations, the surface shape of the sheet material along the shape measurement line is calculated.

The present invention has been completed based on the above-described findings of the present inventors.

In order to achieve the objective, the present invention provides a method for measuring flatness of a sheet material in which a light and dark pattern composed by a light portion and a dark portion is projected onto a surface of the sheet material running in a longitudinal direction, a pattern image is acquired by photographing the light and dark pattern by an image pickup device having an image pickup visual field larger than a width of the sheet material, and the flatness of the sheet material is measured by analyzing the acquired pattern image, comprising the following first to sixth steps:

(1) First step: Using a staggered pattern as the light and dark pattern projected onto the surface of the sheet material, the staggered pattern being composed of light portions arranged in a staggered form at a predetermined preset pitch in a longitudinal direction and a transverse direction, and projecting the staggered pattern onto the surface of the sheet material so that the longitudinal direction of the staggered pattern corresponds to the longitudinal direction of the sheet material and the transverse direction of the staggered pattern corresponds to the width direction of the sheet material.

(2) Second step: Arranging the image pickup device at a position at which the specularly reflected light on the surface of the sheet material of the staggered pattern can be received, and acquiring the pattern image by photographing the staggered pattern by the image pickup device.

(3) Third step: Setting a shape measurement line extending along the longitudinal direction of the staggered pattern at a predetermined position in the acquired pattern image.

(4) Fourth step: Averaging picture element concentrations on a straight line which passes through a picture element on the shape measurement line and extends in the transverse direction of the staggered pattern, and has a length two times or more the transverse preset pitch between the light portions to calculate an average picture element concentration.

(5) Fifth step: Calculating distribution of the average picture element concentrations along the shape measurement line.

(6) Sixth step: Calculating a surface shape of the sheet material along the shape measurement line based on the calculated average picture element concentration distribution, and calculating the flatness of the sheet material based on the calculated surface shape.

In the present invention, the "preset pitch" means a value by which the space between the light portions of the staggered pattern is projected in the image pickup direction in the case where it is assumed that the surface shape of the sheet material onto which the staggered pattern is projected is completely flat. Especially, "longitudinal preset pitch" means a longitudinal space between the light portions adjacent in the staggered form along the longitudinal direction of the staggered pattern. Also, "transverse preset pitch" means a transverse space between the light portions adjacent in the staggered form along the transverse direction of the staggered pattern.

In the sixth step, in order to calculate the surface shape of the sheet material along the shape measurement line based on the distribution of the average picture element concentrations along the shape measurement line, specifically, first, based on the distribution of the average picture element concentrations along the shape measurement line (for example, by applying the publicly known phase analysis method to the distribution of the average picture element concentrations), the distribution $p_m(x)$ of longitudinal pitches between light portions of the staggered pattern along the shape measurement line has only to be calculated. The relationship between the longitudinal pitch $p_m$ between light portions of the staggered pattern and the inclination angle $\theta$ of the sheet material surface can be determined geometrically. Therefore, if the distribution $p_m(x)$ of longitudinal pitches between light portions of the staggered pattern along the shape measurement line is calculated, based on the distribution $p_m(x)$ of longitudinal pitches between light portions and the above-described relationship, the distribution $\theta(x)$ of the inclination angles of the sheet material surface along the shape measurement line can be calculated.

FIG. 4 is a schematic view showing the relationship between the longitudinal pitch $p_m$ between light portions of the staggered pattern and the inclination angle $\theta$ of the sheet material surface. FIG. 4 shows an example in which the sheet material runs in the horizontal direction. In FIG. 4, $\theta$ denotes the inclination angle between the sheet material running direction (horizontal direction) and the sheet material surface, $\alpha$ denotes the angle between the direction perpendicular to the sheet material running direction (vertical direction) and the image pickup direction of the image pickup device, and $\beta$ denotes the angle between the direction perpendicular to the sheet material running direction (vertical direction) and the projection direction of the staggered pattern. Also, $p_m$ denotes the longitudinal pitch between light portions of the staggered pattern in the pattern image acquired for the sheet material, and $p_{m0}$ denotes the value obtained by projecting the pitch $p_m$ in the direction perpendicular to the sheet material running direction (vertical direction). Further, $p_s$ denotes the longitudinal pitch between light portions of the staggered pattern in the pattern image acquired for a reference material that is placed in parallel with the sheet material running direction (placed horizontally) and has a flat surface shape, and $p_{s0}$ denotes the value obtained by projecting the pitch $p_s$ in the direction perpendicular to the sheet material running direction (vertical direction).

Among $\theta$, $\alpha$, $\beta$, $p_m$, $p_{m0}$, $p_s$ and $p_{s0}$, Formulas (4) to (6) hold geometrically.

$$\tan\theta = \frac{(p_{m0}/p_{s0}) - 1}{(p_{m0}/p_{s0})\tan\beta} \quad (4)$$

$$p_{s0} = \frac{p_s}{\cos\alpha} \quad (5)$$

$$p_{s0} = \frac{p_m \cos\theta}{\cos(\alpha - \theta)} \quad (6)$$

Substituting Formulas (5) and (6) into Formula (4), Formula (7) holds.

$$\tan\theta = \frac{(p_m/p_s) - 1}{\tan\alpha + (p_m/p_s)\tan\beta} \quad (7)$$

From Formula (7), Formula (8) holds.

$$\theta = \tan^{-1}\left\{\frac{(p_m/p_s) - 1}{\tan\alpha + (p_m/p_s)\tan\beta}\right\} \quad (8)$$

Therefore, the distribution θ(x) of the inclination angles of the sheet material surface along the shape measurement line can be calculated from Formula (1).

$$\theta(x) = \tan^{-1}\left\{\frac{(p_m(x)/p_S(x))-1}{\tan\alpha + (p_m(x)/p_s(x))\tan\beta}\right\} \quad (1)$$

Therefore, preferably, the method of the present invention further comprises a step of, for a reference material which is placed in parallel with the running direction of the sheet material, on which flatness is measured, and has a flat surface shape, executing the first to fifth steps to calculate the average picture element concentration distribution along the shape measurement line in the pattern image acquired for the reference material, and based on the average picture element concentration distribution, calculating in advance the distribution $p_s(x)$ of longitudinal pitches between light portions of the staggered pattern along the shape measurement line in the pattern image acquired for the reference material; and the sixth step comprises: a step of, based on the average picture element concentration distribution calculated for the sheet material, calculating the distribution $p_m(x)$ of longitudinal pitches between light portions of the staggered pattern along the shape measurement line in the pattern image acquired for the sheet material, and a step of calculating the distribution θ(x) of the inclination angles of the surface of the sheet material along the shape measurement line based on Formula (1), and calculating the surface shape of the sheet material based on the distribution θ(x) of inclination angles of the surface of the sheet material:

$$\theta(x) = \tan^{-1}\left\{\frac{(p_m(x)/p_S(x))-1}{\tan\alpha + (p_m(x)/p_s(x))\tan\beta}\right\} \quad (1)$$

In Formula (1), x denotes a position along the longitudinal direction of the staggered pattern in the pattern image (a position along the longitudinal direction of the sheet material), θ(x) denotes the distribution of inclination angles between the sheet material running direction and the surface of sheet material, α denotes the angle between the direction perpendicular to the sheet material running direction and the image pickup direction of image pickup device, and β denotes the angle between the direction perpendicular to the sheet material running direction and the projection direction of the staggered pattern.

In order to calculate the flatness of the sheet material, the shape measurement lines must be set at least in the central portion in the width direction of the sheet material and in a portion in the vicinity of the edge. However, in the case where the sheet material is, for example, a hot-rolled steel sheet, the sheet material often runs in the state in which meanders and a camber are produced. In this case, even if the width of the sheet material is fixed, the positional relationship between the image pickup device and the sheet material edge changes in the width direction of the sheet material. Therefore, if the shape measurement line is set at a coordinate fixed in the pattern image acquired by the image pickup device, there arises a problem that the shape measurement line is not set correctly in the central portion in the width direction of the sheet material on account of the meanders and camber of the sheet material. In order to avoid this problem, it is preferable that when the shape measurement line is set in the third step, the picture element corresponding to the sheet material edge in the pattern image acquired by the image pickup device is first detected, and the shape measurement line is set with the detected picture element being a reference.

Therefore, preferably, the third step in the method of the present invention comprises: a step of setting an edge detection line extending in the transverse direction of the staggered pattern at a predetermined position in the acquired pattern image; a step of calculating, successively along the edge detection line, standard deviations of picture element concentrations on a straight line which passes through the picture element on the edge detection line and extends along the longitudinal direction of the staggered pattern, and has a length two times or more the longitudinal preset pitch between light portions; a step of, based on the magnitude of the calculated picture element concentration standard deviation, detecting the picture element corresponding to the edge of the sheet material on the edge detection line; and a step of setting the shape measurement line with the detected picture element corresponding to the edge being a reference.

According to the above-described preferable configuration, in the picture element region in which the staggered pattern on the edge detection line is present, both of the light portion and the dark portion are always present on the straight line having a length two times or more the longitudinal preset pitch between the light portions (hereinafter, as appropriate, referred to as a "standard deviation measurement line"). This causes a larger standard deviation of picture element concentrations on the standard deviation measurement line. On the other hand, in the picture element region in which the staggered pattern on the edge detection line is absent, the fact that only the dark portion is present causes a smaller standard deviation of picture element concentrations on the standard deviation measurement line. Therefore, based on the magnitude of picture element concentration standard deviation, the picture element corresponding to the edge of the sheet material on the edge detection line can be detected. If the shape measurement line is set with this picture element corresponding to the edge being a reference, even if the meanders and camber are produced on the sheet material, the shape measurement line can be set correctly at a desired position, for example, in the central portion in the width direction of the sheet material. In the case where the sheet material runs on transfer rolls, by the incidence of light reflected by the transfer roll into the image pickup device, a light picture element region corresponding to the transfer roll may be caused to be present in the pattern image. At this time, if the edge detection line is set at a position at which the picture element region corresponding to the transfer roll is present, there is a fear that the picture element corresponding to the sheet material edge cannot be detected properly. Therefore, in the case where the sheet material runs on the transfer rolls, it is preferable that the edge detection line be set at a position at which the picture element region corresponding to the transfer roll is absent.

When the staggered pattern projected onto the sheet material surface is photographed by the image pickup device, on account of the illuminance unevenness of the light source for projecting the pattern, the inclination angle of the sheet material surface, and the like, in some cases, great unevenness is produced in the picture element concentration of the pattern image acquired by the image pickup device. Specifically, the illuminance unevenness of the light source or the disposition of the image pickup device at a position at which the specularly reflected light reflected by the sheet material surface of the staggered pattern can be received tends to lighten the central portion of staggered pattern. In the case where the unevenness of picture element concentration of the pattern image is large, as in the case where the above-described conventional linear pattern is used, there arises a problem that if the sensitivity of the image pickup device is too high, the staggered pattern is liable to collapse in the picture element region of the central portion in which the picture element concentration of pattern image is high, and on the other hand, if the sensitivity of the image pickup device is too low, the light portion of the staggered pattern is difficult to distinguish in the picture element region of the peripheral portion in which the picture element concentration of pattern image is low.

As the countermeasures for avoiding the above-described problem, it is conceivable that two image pickup devices each having different sensitivity are arranged in parallel so that the image pickup visual fields thereof have portions overlapping with each other, and the shape measurement line is set at the corresponding position in the pattern images acquired by the image pickup devices. In the case where the shape measurement line passes through the picture element region in which the picture element concentration is very high, the surface shape of the sheet material has only to be calculated by using the average picture element concentration distribution along the shape measurement line set in the pattern image acquired by a low-sensitivity image pickup device. On the other hand, in the case where the shape measurement line passes through the picture element region in which the picture element concentration is low, the surface shape of the sheet material has only to be calculated by using the average picture element concentration distribution along the shape measurement line set in the pattern image acquired by a high-sensitivity image pickup device. Specifically, in the average picture element concentration distribution along the shape measurement line set in the pattern image acquired by the high-sensitivity image pickup device, in the case where the number of picture elements in which the concentration saturates is large, the surface shape of the sheet material has only to be calculated by using the average picture element concentration distribution along the shape measurement line set in the pattern image acquired by a low-sensitivity image pickup device. On the other hand, in the average picture element concentration distribution along the shape measurement line set in the pattern image acquired by the high-sensitivity image pickup device, in the case where the number of picture elements in which the concentration saturates is small, the surface shape of the sheet material has only to be calculated by using the average picture element concentration distribution along the shape measurement line set in the pattern image acquired by a high-sensitivity image pickup device.

Therefore, preferably, in the method of the present invention, as the image pickup device, a high-sensitivity image pickup device and a low-sensitivity image pickup device having a sensitivity lower than that of the high-sensitivity image pickup device are used; in the second step, the high-sensitivity image pickup device and the low-sensitivity image pickup device are arranged in parallel so that the image pickup visual fields thereof have portions overlapping with each other; in the third step, the shape measurement line is set at the corresponding position in the pattern images acquired by the high-sensitivity image pickup device and the low-sensitivity image pickup device respectively; and the sixth step comprises: a step of counting the number of picture elements in which the concentration saturates, in the average picture element concentration distribution along the shape measurement line set in the pattern image acquired by the high-sensitivity image pickup device, and a step of, if the number of concentration saturated picture elements is not smaller than a preset predefined threshold value, calculating the surface shape of the sheet material along the shape measurement line based on the average picture element concentration distribution along the shape measurement line set in the pattern image acquired by the low-sensitivity image pickup device, and if the number of concentration saturated picture elements is smaller than the preset threshold value, calculating the surface shape of the sheet material along the shape measurement line based on the average picture element concentration distribution along the shape measurement line set in the pattern image acquired by the high-sensitivity image pickup device.

In the case where the sheet material is a hot-rolled steel sheet, in some cases, the local flatness is too poor, a thin steel sheet rises momentarily, or abnormal scale is formed partially on the steel sheet surface, and therefore there may arise an accident such that the flatness cannot be measured satisfactorily. The control of the finishing mill or the like using an abnormal measured value leads to wrong control, which results in further deterioration in flatness or a trouble on the production line. It is preferable that even if such an abnormal measured value occurs, the control be performed as far as possible, and on the other hand, if abnormalities of measured value occur continuously, the control be halted.

On the other hand, if the measurement range in the longitudinal direction of the hot-rolled steel sheet is about 1 m, the standing waves of sheet observed in the pattern image have about one to three peaks. Therefore, since the measured flatness value measured by using one pattern image varies, it is preferable that a value obtained by averaging the measured flatness values of latest several times be outputted to control the finishing mill and the like.

The measurement response speed necessary for carrying out feedback control to the finishing mill and the like is about 1 second (because of the transfer delay from a flatness measuring instrument to the finishing mill and the like, requirement for a high response speed higher than this speed is meaningless). However, by the recent advances in computer technology, 20 or more of pattern images can be processed for one second, so that even if some degree of averaging is performed, the averaged value can be satisfactorily applied to the control of the finishing mill and the like.

Therefore, preferably, the method of the present invention further comprises: a seventh step of measuring the flatness successively in a plurality of different portions in the longitudinal direction of the sheet material by repeatedly executing the first to sixth steps for the sheet material running in the longitudinal direction; an eighth step of determining whether or not the measured flatness values of preset latest N times (N: integer of 2 or more) succeeded in measurement; and a ninth step of, if among the measured flatness values of the latest N times, the number of times when it is determined that the measurement is successful is not smaller than a preset threshold value, generating a signal indicative of success in measurement, and outputting the average value of the measured flatness value succeeded in measurement among the measured flatness values of the latest N times as a flatness measurement result, and if among the measured flatness values of the latest N times, the number of times when it is determined that the measurement is successful is smaller than the threshold value, generating a signal indicative of failure in measurement.

According to the above-described preferable configuration, even if the flatness measurement fails momentarily for some reason (in the case where the number of times when it is determined that the measurement is successful is not smaller than the threshold value), a signal indicative of success in measurement is generated, and the average value of the measured flatness value succeeded in measurement is outputted as a flatness measurement result. Therefore, if these outputs are inputted to a control unit for controlling the finishing mill and the like, and the control unit carries out control based on this input, the control on the basis of the measured flatness value is carried on continuously. Also, if the measurement fails continuously (in the case where the number of times when it is determined that the measurement is successful is smaller than the threshold value), a signal indicative of failure in measurement is outputted. Therefore, if this output is inputted to the control unit for controlling the finishing mill and the like, the control can be halted suitably. For example, as the number of times N for averaging, 10 times can be exemplified, and as the threshold value, five times can be exemplified.

The determination in the eighth step as to whether or not the measured flatness value succeeded in measurement can be made, for example, by both determinations as to whether or not the edge of sheet material could be detected properly and as to whether or not the surface shape of sheet material along the shape measurement line could be calculated properly. The determination as to whether or not the sheet material edge could be detected properly can be made, for example, by determining whether or not the width and meander amount of sheet material that can be calculated from the coordinate of picture element corresponding to the sheet material edge detected in the pattern image take abnormal values. Also, the determination as to whether or not the surface shape of the sheet material along the shape measurement line could be calculated properly can be made, for example, by determining whether or not the amplitude of the average picture element concentration distribution along the shape measurement line is excessively small.

Therefore, preferably, the eighth step in the method of the present invention comprises: a step of setting two edge detection lines extending in the transverse direction of the staggered pattern at different positions in the longitudinal direction of the staggered pattern in each of the pattern images used to obtain the measured flatness values of the latest N times; a step of detecting the picture element corresponding to the edge of the sheet material on each of the edge detection lines; and a step of, based on a coordinate of the detected picture element corresponding to the edge of the sheet material and the amplitude of the average picture element concentration distribution along the shape measurement line calculated in the fifth step, determining whether or not the measured flatness values of the latest N times succeeded in measurement.

The present invention also provides a method for producing a steel sheet in which method a steel sheet is produced by rolling a slab, which is roughly rolled by a roughing mill, by using a finishing mill train, and thereafter by being cooled by a cooling zone, wherein the flatness of the steel sheet is measured by the above-described flatness measuring method, and based on the measurement result, rolling conditions of the finishing mill or cooling conditions of the cooling zone are controlled.

According to the present invention, even in the case where an image pickup device is arranged at a position at which the specularly reflected light of a light and dark pattern projected onto the surface of a sheet material having a strong specular reflection property can be received, the surface shape of the sheet material can be measured with high accuracy, whereby the flatness of the sheet material can be measured with high accuracy.

BRIEF DESCRIPTION OF THE DRAWINGS

FIG. 1 is a schematic view showing a configuration example of a device for carrying out the grating pattern projection method.
FIG. 2 is an explanatory view for explaining the range in which a camera receives specularly reflected light of a projector projecting light.
[FIG. 3]
FIG. 3 is an explanatory view for explaining various light and dark patterns by comparison.
FIG. 4 is a schematic view showing the relationship between the longitudinal pitch $p_m$ between light portions of the staggered pattern and the inclination angle θ of the sheet material surface.
FIG. 5 is a schematic view showing an outline configuration example of a flatness measuring apparatus for carrying out the flatness measuring method in accordance with the present invention.
FIG. 6 is a schematic view showing the installation state of the flatness measuring apparatus shown in FIG. 5.
FIG. 7 is a graph showing the relationship between $p_m/p_s$ and the inclination angle θ of the surface of the hot-rolled steel sheet under the arrangement condition according to one embodiment of the present invention.
FIG. 9 is a plan view showing another example of staggered pattern formed on the slide composing the projector shown in FIG. 5.
FIG. 10 is a flow chart of processing performed by the image analyzing device shown in FIG. 5.
FIG. 11 is an explanatory view for explaining a method for detecting the edge of the hot-rolled steel sheet and a method for determining the shape measurement line.
FIG. 12 is an explanatory view for explaining the method for calculating the degree of steepness.
FIG. 13 is views showing pattern image examples in the case where the conventional linear pattern is used as a light and dark pattern projected onto the surface of the hot-rolled steel sheet and picture element concentration distributions in the pattern image along the shape measurement line in the central portion in the width direction of the hot-rolled steel sheet and along the shape measurement line in the vicinity of the right-hand side edge thereof.
FIG. 14 is views showing pattern image examples in the case where the staggered pattern is used as a light and dark pattern projected onto the surface of the hot-rolled steel sheet and average picture element concentration distributions in the pattern image along the shape measurement line in the central portion in the width direction of the hot-rolled steel sheet and along the shape measurement line in the vicinity of the right-hand side edge thereof.

[FIG. 15]

FIG. 15 (FIGS. 15A, 15B, 15C and 15D) shows measurement examples of degree of steepness and the like over the overall length of one coil of steel sheet in the case where the conventional linear pattern is used as a light and dark pattern projected onto the surface of the hot-rolled steel sheet.

FIG. 16 (FIGS. 16A, 16B, 16C and 16D) shows measurement examples of degree of steepness and the like over the overall length of one coil of steel sheet in the case where the staggered pattern is used as a light and dark pattern projected onto the surface of the hot-rolled steel sheet S.

FIG. 17 (FIGS. 17A, 17B, 17C and 17D) shows measurement examples of degree of steepness and the like over the overall length of one coil of steel sheet in the case where the staggered pattern is used as a light and dark pattern projected onto the surface of the hot-rolled steel sheet for the hot-rolled steel sheet having material quality of low surface reflectance.

DESCRIPTION OF EMBODIMENTS

One embodiment of the present invention will now be described with reference to the accompanying drawings as appropriate. In the description below, explanation is given by taking as an example the case where the sheet material is a hot-rolled steel sheet, and the flatness (degree of steepness) thereof is measured on the exit of a finishing mill train on a hot-rolled steel sheet production line.

<1. General Configuration of Flatness Measuring Apparatus>

Figure 1:
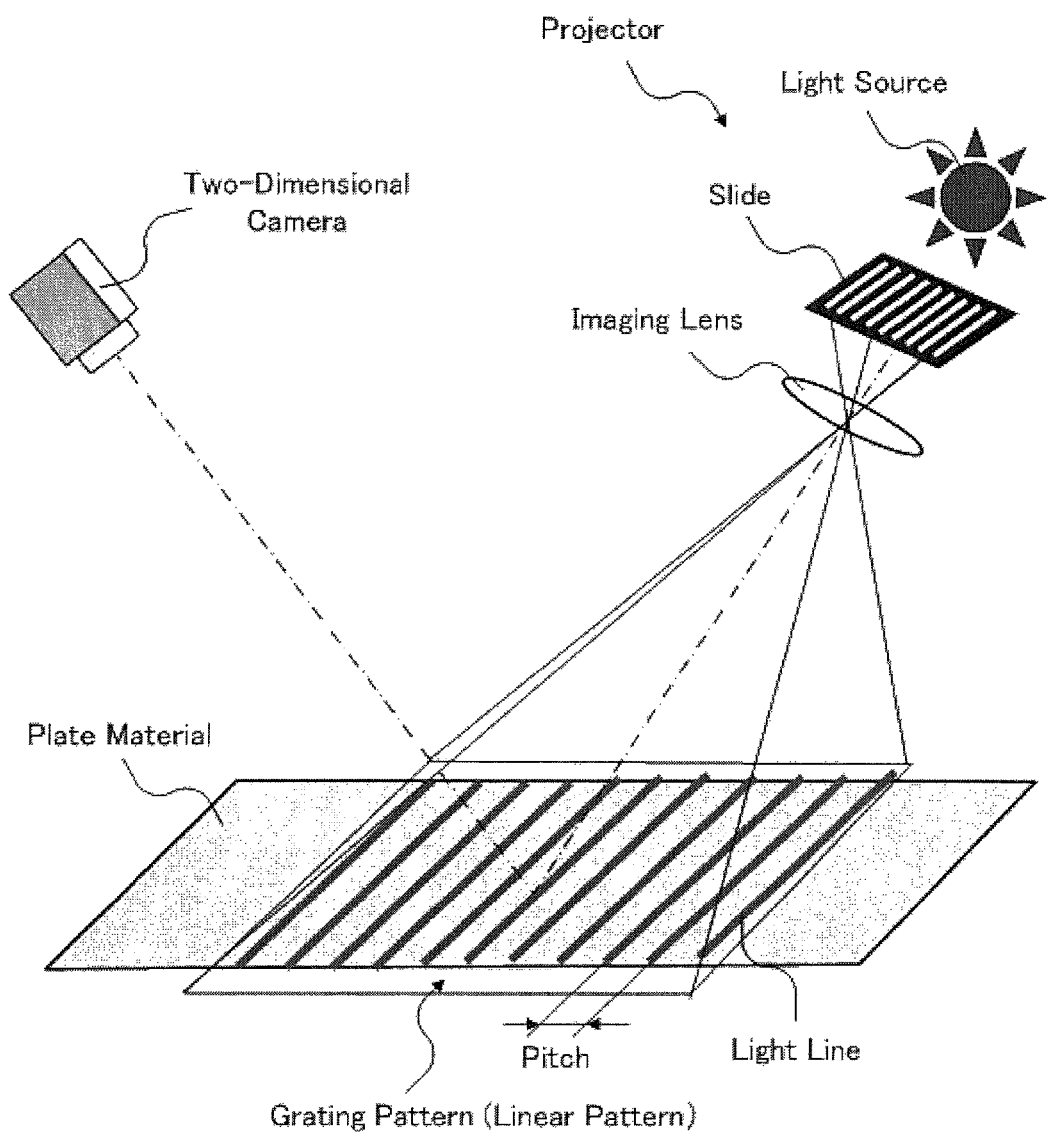
[FIG. 1]
Figure 2:
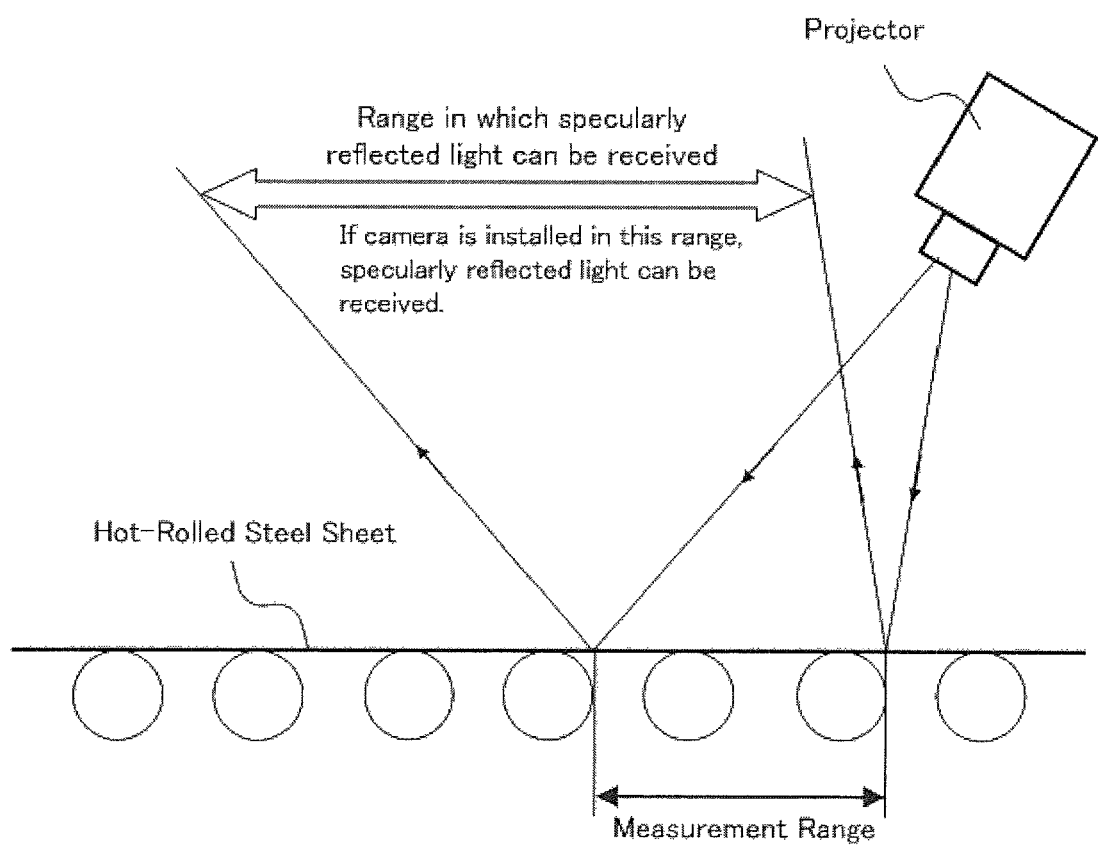
[FIG. 2]
Figure 4:
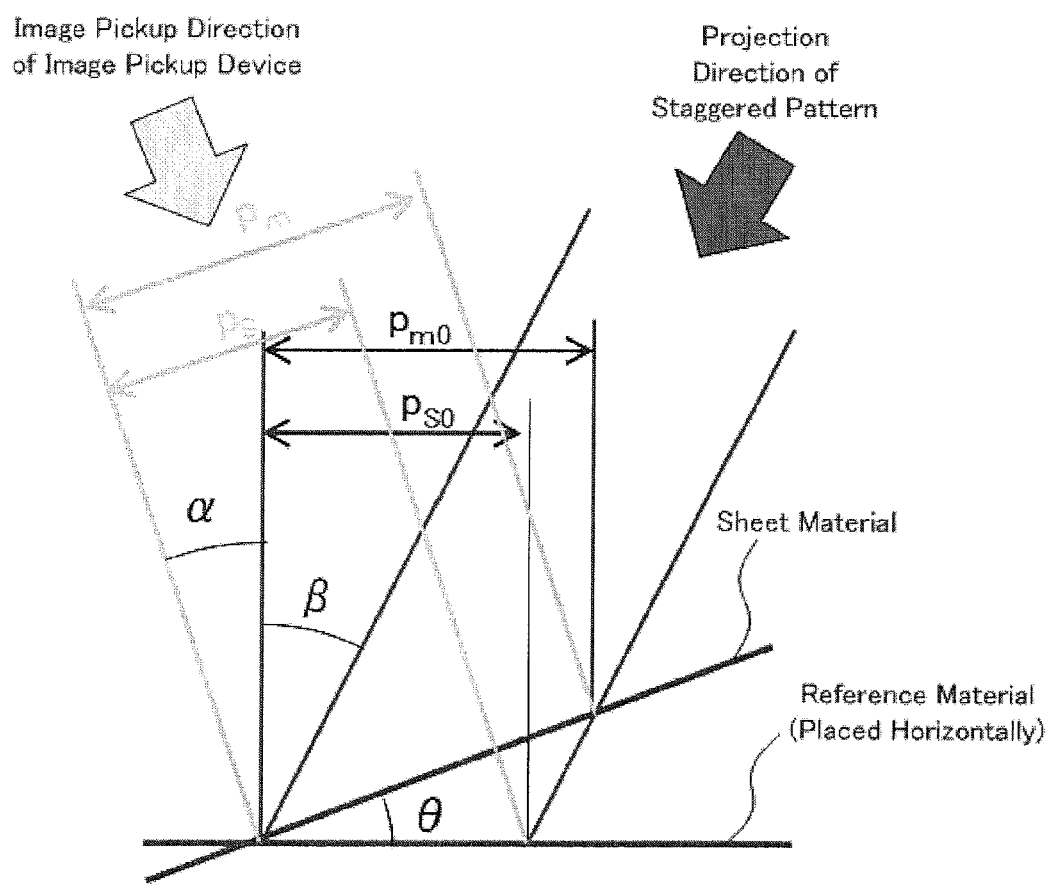
[FIG. 4]
Figure 5:
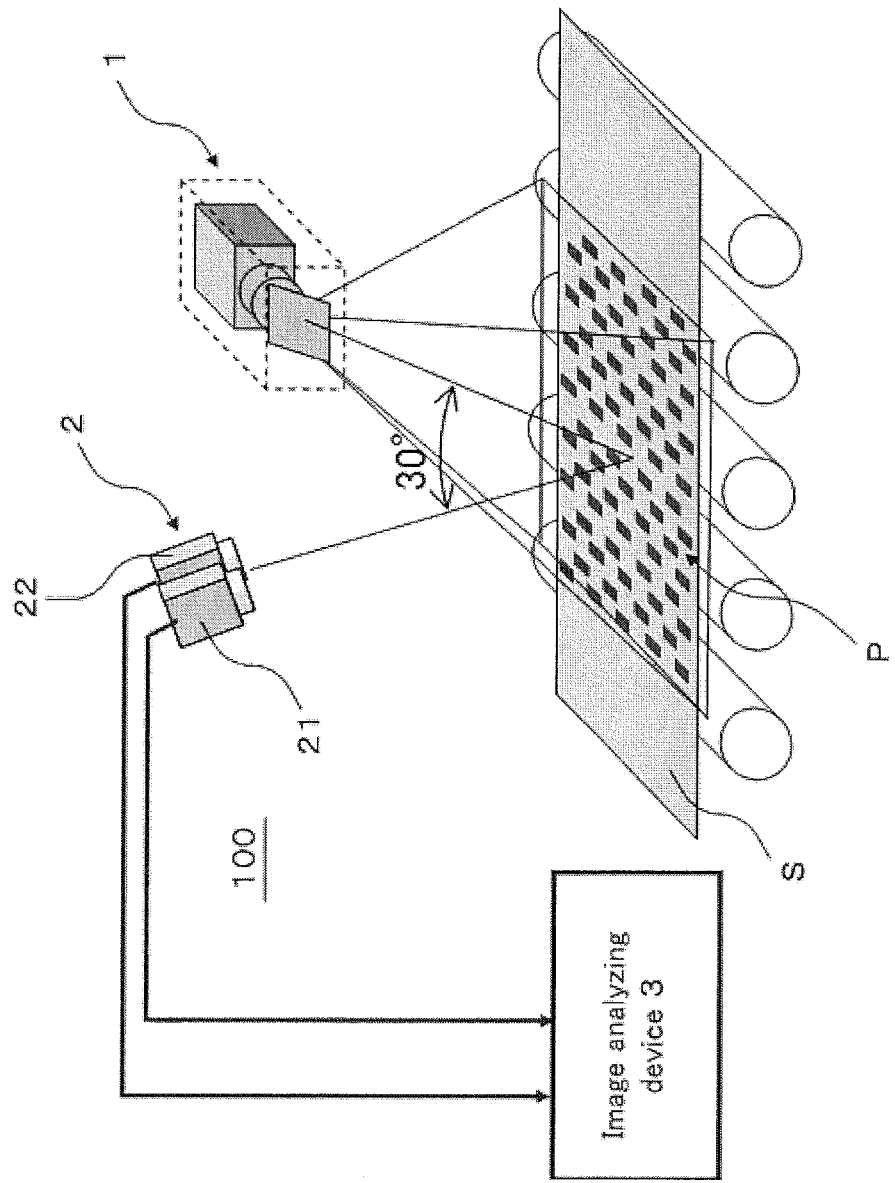
[FIG. 5]
Figure 6:
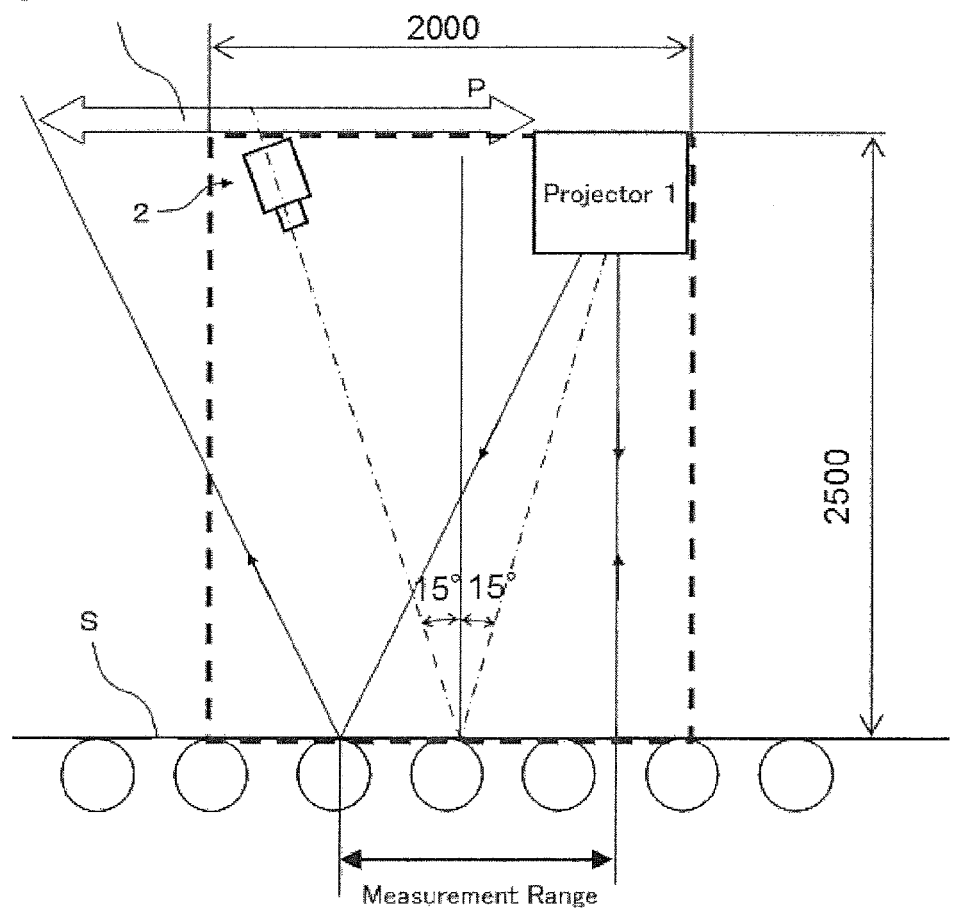
[FIG. 6]

FIG. 5 is a schematic view showing an outline configuration example of a flatness measuring apparatus for carrying out the flatness measuring method in accordance with the present invention. FIG. 6 is a schematic view showing the installation state of the flatness measuring apparatus shown in FIG. 5. As shown in FIGS. 5 and 6, a flatness measuring apparatus 100 of this embodiment includes a projector 1 for projecting a staggered pattern P, which is a light and dark pattern, onto the surface of a hot-rolled steel sheet S running horizontally in the longitudinal direction so that the longitudinal direction of the staggered pattern P corresponds to the longitudinal direction of the hot-rolled steel sheet S and the transverse direction of the staggered pattern P corresponds to the width direction of the hot-rolled steel sheet S; an image pickup device 2 that has an image pickup visual field larger than the width of the hot-rolled steel sheet S, and acquires a pattern image by photographing the staggered pattern P projected onto the surface of the hot-rolled steel sheet S; and an image analyzing device 3 for analyzing the pattern image acquired by the image pickup device 2.

As shown in FIG. 6, the installation space on the exit of the finishing mill train in which the flatness measuring apparatus 100 of this embodiment is installed merely has a length of 2 m in the longitudinal direction of the hot-rolled steel sheet S and a height of 2.5 m in the vertical direction. Therefore, in order to secure at least 1 m of measurement range (image pickup visual field) in the longitudinal direction of the hot-rolled steel sheet S, the image pickup device 2 must be arranged at a position at which the specularly reflected light projected from the projector 1 (the specularly reflected light of the staggered pattern P) can be received. In this embodiment, the staggered pattern P is projected onto the hot-rolled steel sheet S at an angle of 15° (the angle between the vertical direction and the projection direction of the staggered pattern P) from the slantwise upside with respect to the hot-rolled steel sheet S, and this projected staggered pattern P is photographed at an angle of 15° (the angle between the vertical direction and the image pickup direction) from the slantwise upside with respect to the hot-rolled steel sheet S by the image pickup device 2.

Figure 7:
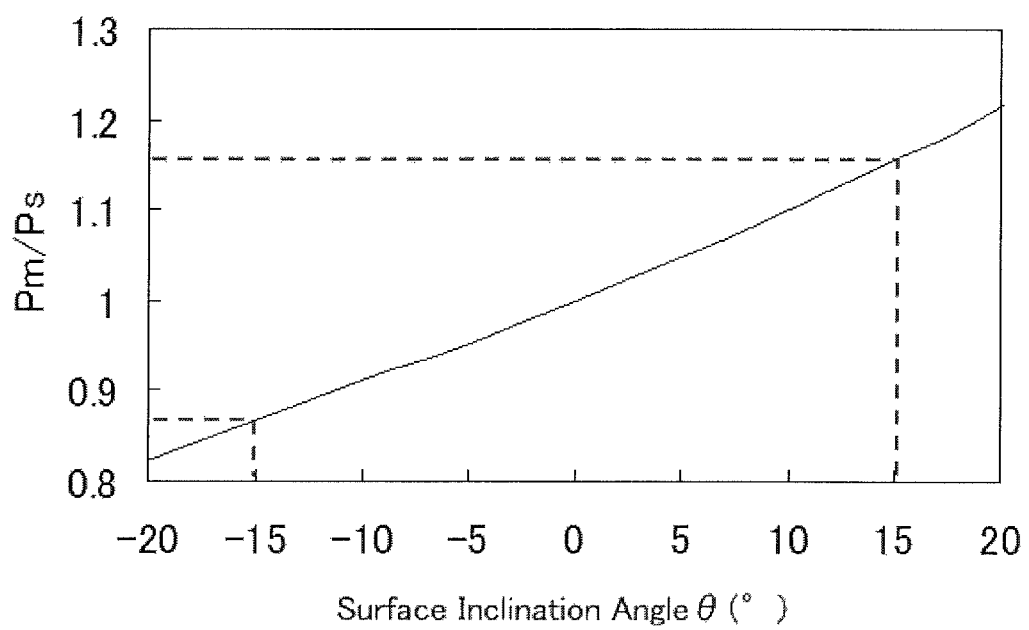
[FIG. 7]

FIG. 7 is a graph showing the relationship between $p_m/p_s$ and the inclination angle θ of the surface of the hot-rolled steel sheet S under the above-described arrangement condition. As described above, $p_m$ denotes a longitudinal pitch between light portions of the staggered pattern P in the pattern image acquired for the hot-rolled steel sheet S, $p_s$ denotes a longitudinal pitch between light portions of the staggered pattern P in the pattern image acquired for a reference material that is placed horizontally and has a flat surface shape, and θ denotes an inclination angle between the horizontal direction and the surface of the hot-rolled steel sheet S. The measurement range of inclination angle θ of the surface of the hot-rolled steel sheet S is determined by the sum of the required flatness (degree of steepness) measurement range and the range of inclination angle of the whole of the hot-rolled steel sheet S that may be formed at the measurement time. In this embodiment, since the required measurement range of degree of steepness is −5% to +5% (corresponding to −9° to +9° if converted into the inclination angle of the surface of the hot-rolled steel sheet S), and additionally considering the allowance of a change in inclination angle of the whole of the hot-rolled steel sheet S caused by the fluttering of the hot-rolled steel sheet S, the measurement range of inclination angle θ of the surface of the hot-rolled steel sheet S is made −15° to +15°. FIG. 7 reveals that if the inclination angle of the surface of the hot-rolled steel sheet S changes in the range of −15° to +15°, $p_m/p_s$ changes in the range of 0.85 to 1.15.

<2. Configuration of Projector>

In this embodiment, as a light source composing the projector 1, a metal halide lamp having a rated power of 2.5 kW is used. The light emitted from this lamp passes through a slide and an imaging lens arranged in front of the lamp and is projected onto the surface of the hot-rolled steel sheet S at an imaging magnification of about ×20. The distance from the projector 1 to the surface of the hot-rolled steel sheet S is about 2 m, and the dimensions of the projected staggered pattern are 1400 mm in the longitudinal direction and 1800 mm in the transverse direction. On the slide, the staggered pattern is formed by depositing Cr on a quartz glass substrate. The portion on which Cr is deposited is the dark portion of the staggered pattern, and the portion on which Cr is not deposited is the light portion of the staggered pattern.

Figure 8B:
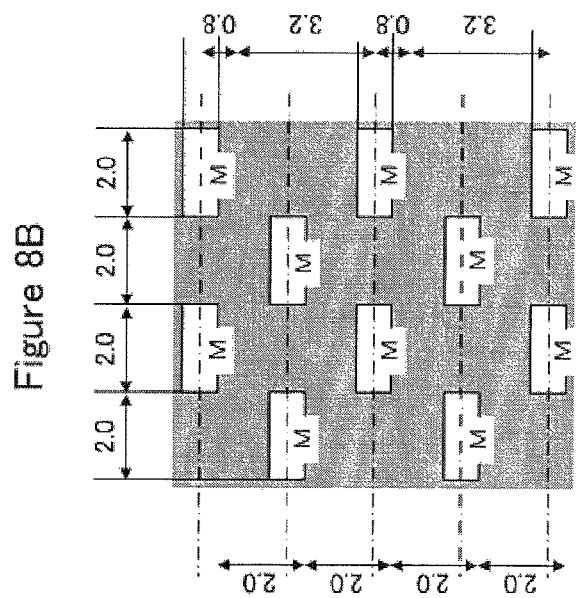
[FIG. 8]
FIG. 8 (FIGS. 8A and 8B) is a plan view showing one example of staggered pattern formed on the slide composing the projector shown in FIG. 5.
Figure 8A:
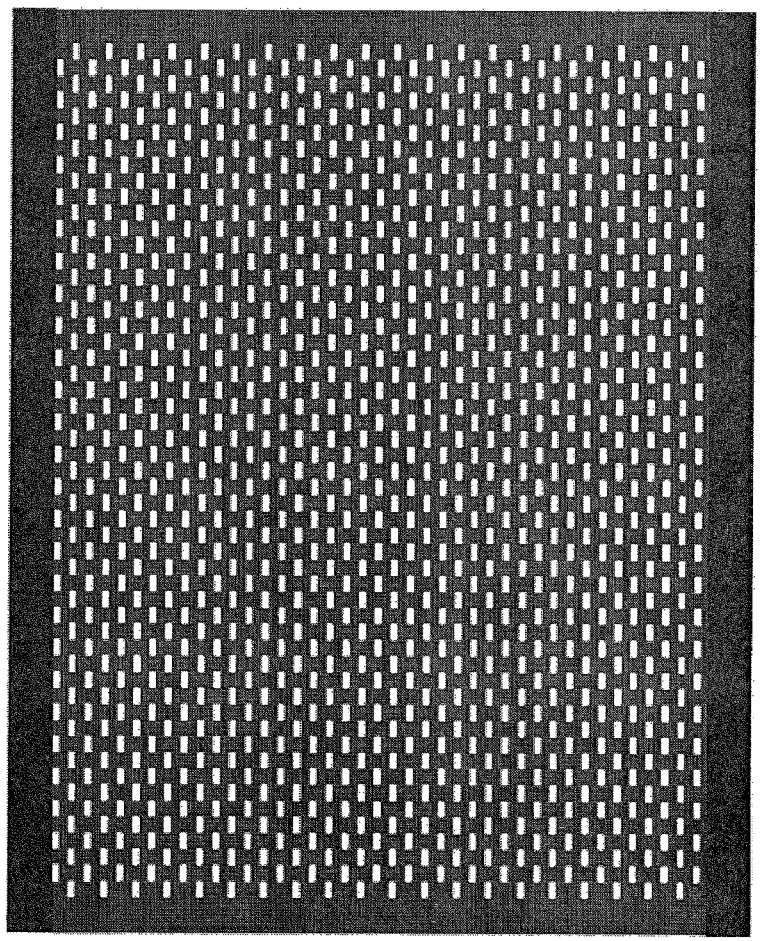

FIG. 8 (FIGS. 8A and 8B) is a plan view showing one example of staggered pattern formed on the slide composing the projector, FIG. 8A being a general view, and FIG. 8B being a partial enlarged view. As shown in FIG. 8, on the slide, light portions M are arranged in a staggered form at a pitch of 2 mm in the longitudinal direction and the transverse direction respectively. As described above, the imaging magnification is about ×20, so that onto the surface of the hot-rolled steel sheet S is projected the staggered pattern P in which the light portions M are arranged in a staggered form at a 40-mm pitch in the longitudinal direction and the transverse direction respectively (that is, the longitudinal preset pitch $P_L$=40 mm, the transverse preset pitch $P_W$=40 mm).

Figure 9:
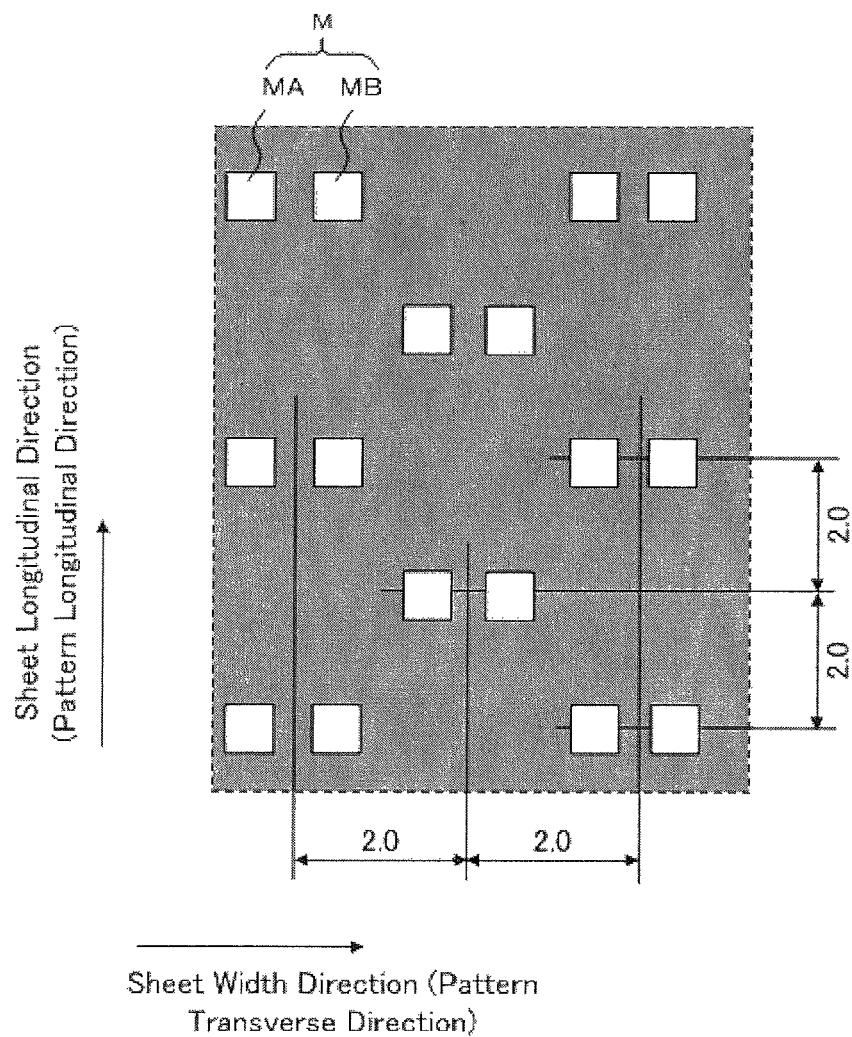
[FIG. 9]

The staggered pattern is not limited to the pattern shown in FIG. 8, and can be made a staggered pattern in which, for example, one light portion M is divided into two elements MA and MB without changing the pitch of the light portion M as shown in FIG. 9. Also, the influence of illuminance unevenness of the projector 1 can be restrained by devising so that the size of the light portion M is changed partially. In this embodiment, the illuminance in the vicinity of the surface of the hot-rolled steel sheet S is about 6000 Lx in the vicinity of the optical axis of the projector 1 and about 3000 Lx in the vicinity of the edge of the hot-rolled steel sheet M. In this embodiment, the whole of the projector 1 is housed in a dustproof box made of a stainless steel because the projector 1 is installed at the site at which dust particles and foggy waterdrops scatter in large amounts. Also, the projector 1 has a construction such that air is supplied into the dustproof box by using a large-sized blower and is let to blow off to the outside through an opening for projecting the staggered pattern to prevent dust particles and foggy waterdrops from intruding into the dustproof box through the opening <3. Configuration of Image Pickup Device>

In this embodiment, as the image pickup device 2, a two-dimensional CCD camera is used which has a SVGA-size image sensor (the image sensor has 788 light-receiving elements in the transverse direction, 580 light-receiving elements in the longitudinal direction) and outputs 40 image signals per second in a progressive system. This CCD camera is configured so that a plurality of cameras can pick up images synchronously by means of a synchronization signal sent from the outside. In this embodiment, as the image pickup device 2, two CCD cameras 21 and 22 described above are used. The CCD cameras 21 and 22 are arranged in parallel so that the image pickup visual fields thereof have portions overlapping with each other, and by the adjustment of lens stop and gain of respective cameras, the sensitivity is set at 1:4 (hereinafter, as appropriate, the CCD camera having lower sensitivity is referred to as the low-sensitivity image pickup device 21, and the CCD camera having higher sensitivity is referred to as the high-sensitivity image pickup device 22).

In this embodiment, the exposure time of the image pickup device 2 is set at 2.5 msec so that the surface shape of the hot-rolled steel sheet S that is rolled and coiled at a high speed of 1500 mpm at the maximum can be measured without blurring. Also, the image pickup device 2 of this embodiment is provided with a band-pass filter allowing only blue-green color to penetrate in front of the lens so that the staggered pattern can be photographed clearly without being affected by the radiation light radiated from the surface of the hot-rolled steel sheet S even when the hot-rolled steel sheet S having a temperature of 950° C. is measured. The image pickup device 2 of this embodiment as well is, like the projector 1, housed in a dustproof box made of a stainless steel, and is air purged by pressurized air to prevent the lens from being stained. The image pickup device 2 of this embodiment has an image pickup visual field of about 1800 mm in the width direction of the hot-rolled steel sheet S, so that the transverse resolution of the pattern image acquired by the image pickup device 2 is about 2.3 mm per picture element.

<4. Configuration of Image Analyzing Device>

The image analyzing device 3 of this embodiment has a configuration such that a program for executing the later-described processing (hereinafter, referred to as a flatness analyzing program) is installed in a general-purpose personal computer (CPU: Core2Duo processor of 2.4-GHz clock frequency, OS: Windows (registered trademark)). The image analyzing device 3 is configured so as to capture image signals outputted from the low-sensitivity image pickup device 21 and the high-sensitivity image pickup device 22 in a memory simultaneously at 256 gradation (8 bits) by using an incorporated multichannel image capturing board. The image data (pattern image) captured in the memory of the image analyzing device 3 is analyzed by the flatness analyzing program, and the measured flatness value as an analysis result is outputted to the monitor screen of the image analyzing device 3 and a host control unit (a control unit for controlling the finishing mill and the like).

<5. Processing Details of Flatness Analyzing Program>

Figure 10:
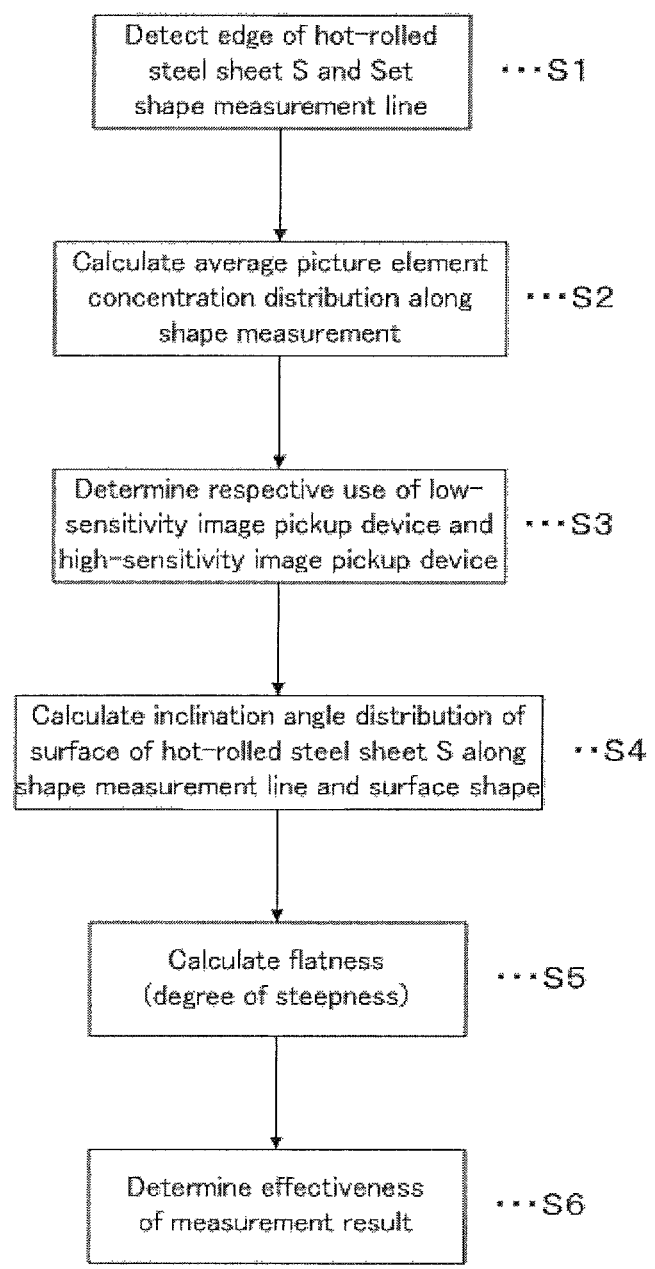
[FIG. 10]

The image analyzing device 3 performs processing on the pattern image photographed and acquired by the image pickup device 2 by the procedure shown in FIG. 10 by using the installed flatness analyzing program. Hereunder, the processing is explained successively.

<5-1. Processing for Detection of Edge of Hot-Rolled Steel Sheet and for Setting of Shape Measurement Lines (S1 in FIG. 10)>

Figure 11:
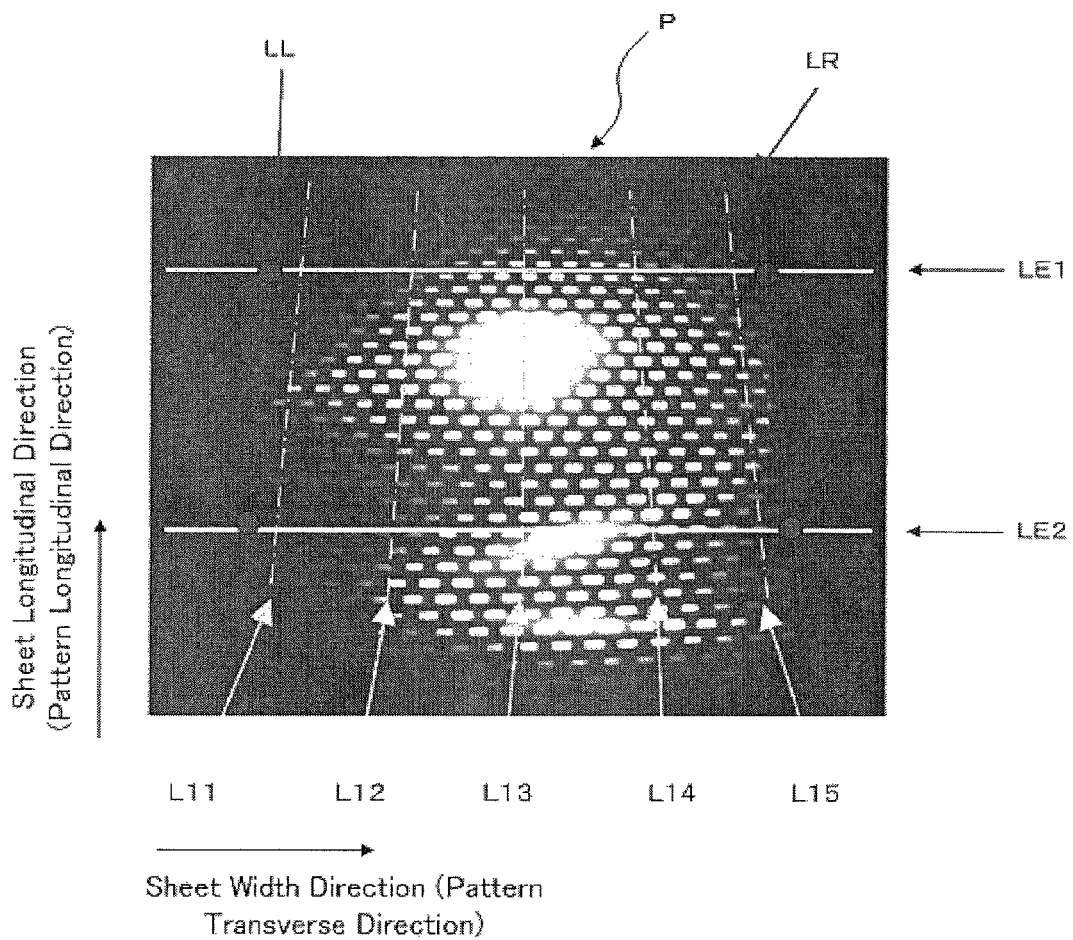
[FIG. 11]

FIG. 11 is an explanatory view for explaining a method for detecting the edge of the hot-rolled steel sheet and a method for determining the shape measurement line. In detecting the edge of the hot-rolled steel sheet S, first, edge detection lines LE1 and LE2 extending in the transverse direction of the staggered pattern P at predetermined positions (two different positions in the longitudinal direction of the staggered pattern P) are set in the pattern image acquired by the high-sensitivity image pickup device 22.

Next, the standard deviations of picture element concentrations on a straight line that passes through the picture element on the edge detection line LE1 and extends along the longitudinal direction of the staggered pattern P, and has a length (100 mm in this embodiment) two times or more the longitudinal preset pitch (in this embodiment, the longitudinal preset pitch $P_L$=40 mm) between the light portions are calculated successively along the edge detection line LE1. Based on the magnitude of the calculated picture element concentration standard deviation, picture elements E11 and E12 corresponding to the edge of the hot-rolled steel sheet S are detected on the edge detection line LE1. Specifically, for example, the distribution of the picture element concentration standard deviations along the edge detection line LE1 has only to be differentiated along the edge detection line LE1, and the picture element E11 in which the differentiated intensity is at the maximum and the picture element E11 in which the differentiated intensity is at the minimum have only to be detected as picture elements corresponding to the edge of the hot-rolled steel sheet S. For the edge detection line LE2 as well, likewise, based on the magnitude of the calculated picture element concentration standard deviation calculated successively along the edge detection line LE2, picture elements E21 and E22 corresponding to the edge of the hot-rolled steel sheet S are detected on the edge detection line LE2. By the above-described processing, the straight line passing through the picture elements E11 and E21 and the straight line passing through the picture elements E12 and E22 are detected as estimated edges LL and LR of the steel sheet S, respectively.

Based on the coordinates of the detected picture elements E11 and E12 and the transverse resolution of pattern image (in this embodiment, about 2.3 mm per picture element), the width of the hot-rolled steel sheet S on the edge detection line LE1 can be calculated. Likewise, based on the coordinates of the detected picture elements E21 and E22 and the transverse resolution of pattern image, the width of the hot-rolled steel sheet S on the edge detection line LE2 can be calculated. In the case where the difference between the width of the hot-rolled steel sheet S on the edge detection line LE1 and the width of the hot-rolled steel sheet S on the edge detection line LE2 is large (for example, 10 mm or larger), it can be determined that the edge of the hot-rolled steel sheet S could not be detected properly. Also, from the coordinates of the detected picture elements E11 and E12, the coordinate of the central portion of the hot-rolled steel sheet S on the edge detection line LE1 can be calculated. Likewise, the coordinate of the central portion of the hot-rolled steel sheet S on the edge detection line LE2 can be calculated from the coordinates of the detected picture elements E21 and E22. Based on the difference between the coordinate of the central portion of the hot-rolled steel sheet S on the edge detection line LE1 and the coordinate of the central portion of the hot-rolled steel sheet S on the edge detection line LE2 and the transverse resolution of pattern image, the meander amount of the hot-rolled steel sheet S can be calculated. If this meander amount is larger than a predefined threshold value, it can be determined that the edge of the hot-rolled steel sheet S could not be detected properly.

The shape measurement lines are determined with the picture elements E11 to E22 corresponding to the edge detected as described above being references (with a left-hand side estimated edge LL passing through the picture elements E11 and E21 and a right-hand side estimated edge LR passing through the picture elements E12 and E22 being references), and are set in the pattern image acquired by the high-sensitivity image pickup device 22. Specifically, in this embodiment, there are set a total of five shape measurement lines: a shape measurement line L11 in the vicinity of the left-hand side edge of the hot-rolled steel sheet S (on the inside by 75 mm from the left-hand side estimated edge LL), a shape measurement line L12 on the inside by a length corresponding to one-fourth of the width of the hot-rolled steel sheet S from the left-hand side edge of the hot-rolled steel sheet S (on the inside by a length corresponding to one-fourth of the width of the hot-rolled steel sheet S from the left-hand side estimated edge LL), a shape measurement line L13 in the central portion in the width direction of the hot-rolled steel sheet S, a shape measurement line L14 on the inside by a length corresponding to one-fourth of the width of the hot-rolled steel sheet S from the right-hand side edge of the hot-rolled steel sheet S (on the inside by a length corresponding to one-fourth of the width of the hot-rolled steel sheet S from the right-hand side estimated edge LR), and a shape measurement line L15 in the vicinity of the right-hand side edge of the hot-rolled steel sheet S (on the inside by 75 mm from the right-hand side estimated edge LR).

The positional relationship between the coordinates in the pattern image acquired by the high-sensitivity image pickup device 22 and the coordinates in the pattern image acquired by the corresponding low-sensitivity image pickup device 21 is determined in advance. Thereby, for the pattern image acquired by the low-sensitivity image pickup device 21, the shape measurement lines can be set at positions corresponding to the shape measurement lines L11 to L15 set for the pattern image acquired by the high-sensitivity image pickup device 22.

<5-2. Processing for Calculation of Average Picture Element Concentration Distribution Along Shape Measurement Line (S2 in FIG. 10)>

In this processing, in the pattern image acquired by each of the low-sensitivity image pickup device 21 and the high-sensitivity image pickup device 22, the picture element concentrations on a straight line that passes through the picture elements on the shape measurement lines L11 to L15 and extends in the transverse direction of the staggered pattern, and has a length two times or more the transverse preset pitch between the light portions (in this embodiment, the transverse preset pitch $P_W$=40 mm) are averaged, whereby the average picture element concentration is calculated. In this embodiment, since the transverse resolution of the pattern image is about 2.3 mm per picture element as described above, the length of the straight line on which the picture element concentrations are averaged has only to be 35 picture elements or more. Therefore, in this embodiment, the length of the straight line on which the picture element concentrations are averaged is made 40 picture elements, and thereby the distribution of the average picture element concentrations along each of the shape measurement lines L11 to L15 is calculated. Also, the x coordinate (the position along the longitudinal direction of the staggered pattern in the pattern image) on each of the shape measurement lines L11 to L15 calculates the average picture element concentration distribution in the range of 50 to 561 in picture element units (that is, 512 pieces of average picture element data).

<5-3. Processing for Determination of Respective Use of Low-Sensitivity Image Pickup Device and High-Sensitivity Image Pickup Device (S3 in FIG. 10)>

In this processing, in the average picture element concentration distribution along each of the shape measurement lines L11 to L15 set in the pattern image acquired by the high-sensitivity image pickup device 22, the number of picture elements in which the concentration saturates is counted. Specifically, in this embodiment, if the concentration exceeds 250, it is thought that the concentration saturates, and the number of picture elements (the number of concentration saturated picture elements) is counted. As the result, if the number of concentration saturated picture elements is not smaller than a preset predefined threshold value, the average picture element concentration distribution along the shape measurement line set in the pattern image acquired by the low-sensitivity image pickup device 21 is used (as described later, the surface shape of the hot-rolled steel sheet S along the shape measurement line is calculated by using this average picture element concentration distribution). On the other hand, if the number of concentration saturated picture elements is smaller than the preset threshold value, the average picture element concentration distribution along the shape measurement line set in the pattern image acquired by the high-sensitivity image pickup device 22 is used. Specifically, for example, in the average picture element concentration distribution along the shape measurement line L11 set in the pattern image acquired by the high-sensitivity image pickup device 22, if the number of concentration saturated picture elements is not smaller than the threshold value, the average picture element concentration distribution along the shape measurement line L11 set in the pattern image acquired by the low-sensitivity image pickup device 21 is used. Also, for example, in the average picture element concentration distribution along the shape measurement line L13 set in the pattern image acquired by the high-sensitivity image pickup device 22, if the number of concentration saturated picture elements is smaller than the threshold value, the average picture element concentration distribution along the shape measurement line L13 set in the pattern image acquired by the low-sensitivity image pickup device 21 is used.

<5-4. Processing for Calculation of Inclination Angle Distribution of Hot-Rolled Steel Sheet Along Shape Measurement Line and Surface Shape (S4 in FIG. 10)>

In this processing, based on the average picture element concentration distribution along the shape measurement lines L11 to L15 calculated as described above for the hot-rolled steel sheet S, on which flatness is measured, the distribution $p_m(x)$ of longitudinal pitch between light portions of the staggered pattern P along the shape measurement lines L11 to L15 is calculated.

On the other hand, for the reference material that is placed horizontally and has a flat surface shape as well, the same processing as described above is performed, and the average picture element concentration distribution along the shape measurement lines L11 to L15 in the pattern image acquired on the reference material is calculated. Based on the average picture element concentration distribution along the shape measurement lines L11 to L15, the distribution $p_s(x)$ of longitudinal pitch between light portions of the staggered pattern along the shape measurement lines L11 to L15 is calculated in advance.

As a method for calculating the distributions $p_m(x)$ and $p_s(x)$ of longitudinal pitch between light portions based on the average picture element concentration distribution, various methods are conceivable. In this embodiment, the phase analysis method explained below is applied.

Hereunder, the phase analysis method applied to the above-described average picture element concentration distribution will be explained.

The average picture element concentration distribution obtained for the hot-rolled steel sheet S, on which flatness is measured, is taken as f(x). If, by applying the frequency analysis method such as the Fourier transform method to this f(x), only a space frequency component corresponding to the assumed change width (for example, −5% to +5%) of the longitudinal pitch between light portions of the staggered pattern is drawn out of f(x), the distribution $f_s(x)$ represented by Formula (9) is obtained. Since this $f_s(x)$ includes only the distribution of the longitudinal pitches between light portions of the projected staggered pattern as a periodic component, the distribution of the longitudinal pitches can be determined by analyzing a phase component $\phi(x)$.

$$f_S(x) = A(x)\sin\phi(x) \qquad (9)$$

For the analysis of phase component, for example, Hilbert transformation can be used. The Hilbert transformation is transformation into a waveform of the same amplitude, in which the phase shifts by $\pi/2$ (90° with respect to the original waveform. In the calculation method for accomplishing the Hilbert transformation, the coefficient of negative frequency portion of $F_s(k)$ obtained by subjecting $f_s(x)$ to discrete Fourier transform is replaced with 0, and the fact that the result of discrete reverse Fourier transform is $f_s(x)+if_H(x)$ is utilized. Since the phase of the obtained $f_H(x)$ shifts by $\pi/2$ with respect to $f_S(x)$, $f_S(x)$ is represented by Formula (10).

$$f_H(x) = A(x)\sin\{\phi(x) - \frac{\pi}{2}\} = -A(x)\cos\phi(x) \qquad (10)$$

Therefore, the result of calculation of arc tangent (inverse tangent function) of $f_S(x)/f_H(x)$ is equal to $-\phi(x)$, which is a phase component, as shown in Formula (11).

$$\tan^{-1}\left\{\frac{f_S(x)}{f_H(x)}\right\} = -\tan^{-1}\left\{\frac{A(x)\sin\phi(x)}{A(x)\cos\phi(x)}\right\} = -\phi(x) \qquad (11)$$

Since the obtained $\phi(x)$ has been wrapped (folded each $\pi$), $\pi$ is added or subtracted at each folding point (unwrapping processing) to produce a continuous waveform. Also, as shown in Formula (12), the square sum square roots of $f_S(x)$ and $f_H(x)$ are calculated, and thereby the amplitude $A(x)$ of $f_S(x)$ can be determined.

$$\sqrt{\{f_S(x)\}^2 + \{f_H(x)\}^2} = \sqrt{\{A(x)\sin(\phi(x))\}^2 + \{A(x)\cos(\phi(x))\}^2} = A(x) \qquad (12)$$

Herein, since $d\phi(x)/dx$, which is the differential of phase component $\phi(x)$, is equal to a value obtained by multiplying the space frequency distribution by $2\pi$, the longitudinal pitch $p_m(x)$ between light portions of the staggered pattern can be determined by Formula (13).

$$p_m(x) = 2\pi\left(\frac{d\phi(x)}{dx}\right)^{-1} \qquad (13)$$

For the average picture element concentration distribution obtained for the reference material that is placed horizontally and has a flat surface shape, as well, the same analysis as described above is performed, whereby the longitudinal pitch $p_s(x)$ between light portions of the staggered pattern can be determined.

Next, in this processing, based on the distributions $p_m(x)$ and $p_s(x)$ of longitudinal pitches between light portions of the staggered pattern, which are calculated as described above and Formula (1), the distribution $\theta(x)$ of inclination angles of the surface of the hot-rolled steel sheet S along the shape measurement lines L11 to L15 is calculated.

$$\theta(x) = \tan^{-1}\left\{\frac{(p_m(x)/p_S(x)) - 1}{\tan\alpha + (p_m(x)/p_S(x))\tan\beta}\right\} \qquad (1)$$

In Formula (1), x denotes a position along the longitudinal direction of the staggered pattern in the pattern image (a position along the longitudinal direction of the sheet material), $\theta(x)$ denotes the distribution of inclination angles between the horizontal direction and the surface of the sheet material, $\alpha$ denotes the angle between the vertical direction and the image pickup direction of the image pickup device (15° in this embodiment), and $\beta$ denotes the angle between the vertical direction and the projection direction of the staggered pattern (15° in this embodiment).

Finally, in this processing, the inclination angles of the surface of the hot-rolled steel sheet S along each of the shape measurement lines L11 to L15, which are calculated as described above, are integrated along each of the shape measurement lines L11 to L15, whereby the surface shape of the hot-rolled steel sheet S along each of the shape measurement lines L11 to L15 can be calculated.

The determination as to whether or not the surface shape of the hot-rolled steel sheet S along each of the shape measurement lines L11 to L15 could be calculated properly can be made, for example, by determining whether or not the amplitude of the average picture element concentration distribution along each of the shape measurement lines L11 to L15 is excessively small. Specifically, the number of picture elements in which the amplitude is smaller than the preset threshold value among the amplitudes $A(x)$ calculated by Formula (12) by the above-described phase analysis of the average picture element concentration distribution f(x) is counted. If the number of picture elements is smaller than a predetermined number, it is determined that the surface shape of the hot-rolled steel sheet S could not be calculated properly. If the number of picture elements is not smaller than the predetermined number, it can be determined that the surface shape of the hot-rolled steel sheet S could be calculated properly.

<5-5. Processing for Calculation of Flatness (Degree of Steepness) (S5 in FIG. 10)>

In this processing, based on the surface shape of the hot-rolled steel sheet S along each of the shape measurement lines L11 to L15, which is calculated as described above, the degree of steepness is calculated. In calculating the degree of steepness, first, based on the surface length in a certain section to be measured along each of the shape measurement lines L11 to L15 and the direct distance therebetween, the elongation percentage on each of the shape measurement lines L11 to L15 is calculated. Then, the difference in elongation percentage $\Delta\epsilon$, which is a difference between the elongation percentage $\epsilon_{CENT}$ on the shape measurement line L13 in the central portion in the width direction of the hot-rolled steel sheet S and the elongation percentage $\epsilon_{EDGE}$ on other shape measurement lines L11, L12, L14 and L15, is calculated (refer to Formula (2)). Then, based on this difference in elongation percentage $\Delta\epsilon$ and Formula (3), the degree of steepness $\lambda$ is calculated.

Figure 12:
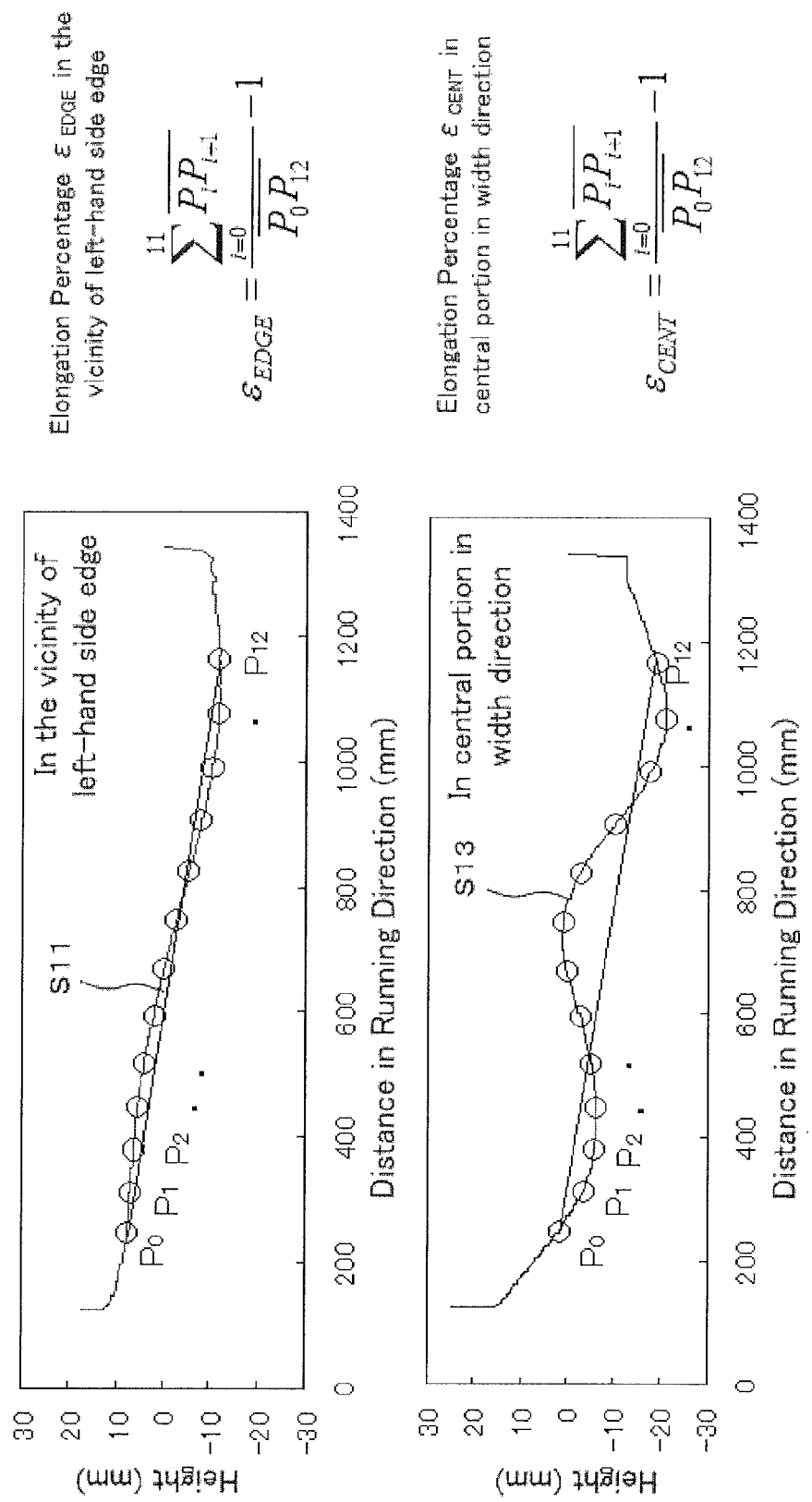
[FIG. 12]

Hereunder, the case where the degree of steepness is determined based on the surface shape along the shape measurement line L11 in the vicinity of the left-hand side edge and the shape measurement line L13 in the central portion in the width direction is explained specifically with reference to FIG. 12.

FIG. 12 is an explanatory view for explaining the method for calculating the degree of steepness. The elongation percentage $\epsilon_{EDGE}$ on the shape measurement line L11 is calculated by the formula in FIG. 12 based on the surface length in a section in which a surface shape S11 of the hot-rolled steel sheet S is measured along the shape measurement line L11 and the direct distance therebetween. Likewise, the elongation percentage $\epsilon_{CENT}$ on the shape measurement line L13 is calculated by the formula in FIG. 12 based on the surface length in a section in which a surface shape S13 of the hot-rolled steel sheet S is measured along the shape measurement line L13 and the direct distance therebetween. In the example shown in FIG. 12, to restrain the influence of minute measurement noise, the section to be measured is divided into 12 subsections by points $P_0$ to $P_{12}$, and the surface lengths of the surface shapes S11 and S13 are calculated by polygonal line approximation. The difference in elongation percentage $\Delta\epsilon$, which is the difference between the elongation percentage $\epsilon_{CENT}$ on the shape measurement line L13 and the elongation percentage $\epsilon_{EDGE}$ on the shape measurement line L11, is calculated, and based on this difference in elongation percentage $\Delta\epsilon$ and Formula (3), the degree of steepness $\lambda$ is calculated.

<5-6. Processing for Determination of Effectiveness of Measurement Result (S6 in FIG. 10)>

In this processing, the flatness (degree of steepness) is measured successively in a plurality of different portions in the longitudinal direction of the hot-rolled steel sheet S as described above, and it is determined whether or not the measured flatness values of preset latest N times (N: integer of 2 or more) succeeded in measurement. In this embodiment, the determination as to whether or not the measured flatness values succeeded in measurement is made by both determinations as to whether or not the edge of the hot-rolled steel sheet S could be detected properly and as to whether or not the surface shape of the hot-rolled steel sheet S along the shape measurement line could be calculated properly. That is, only when the edge of the hot-rolled steel sheet S could be detected properly and the surface shape of the hot-rolled steel sheet S along the shape measurement line could be calculated properly, it is determined that the measured flatness values succeeded in measurement. As described above, the determination as to whether or not the edge of the hot-rolled steel sheet S could be detected properly is made by determining whether or not the difference between the width of the hot-rolled steel sheet S on the edge detection line LE1 and the width of the hot-rolled steel sheet S on the edge detection line LE2 is large and whether or not the meander amount of the hot-rolled steel sheet S is larger than the predefined threshold value. Also, for the determination as to the surface shape of the hot-rolled steel sheet S along the shape measurement line could be calculated properly, as described above, the number of picture elements in which the amplitude is smaller than the preset threshold value among the amplitudes A(x) calculated by Formula (12) is counted, if the number of picture elements is smaller than the predetermined number, it is determined that the surface shape of the hot-rolled steel sheet S could not be calculated properly, and if the number of picture elements is not smaller than the predetermined number, it is determined that the surface shape of the hot-rolled steel sheet S could be calculated properly.

Next, in this processing, if among the measured flatness values of the latest N times, the number of times when it is determined that the measurement is successful is not smaller than a preset threshold value M, a signal indicative of success in measurement (a signal indicative that the measurement result is effective) is generated to the control unit for controlling the finishing mill and the like, and among the measured flatness values of the latest N times, the average value of the measured flatness values succeeded in measurement is outputted to the control unit as a flatness measurement result. On the other hand, if the number of times when it is determined that the measurement is successful is smaller than the threshold value M, a signal indicative of failure in measurement (a signal indicative that the measurement result is ineffective) is generated to the control unit.

In this embodiment, N is set at 10. According to the image analyzing device 3 of this embodiment, since 20 pattern images can be processed for one second, N=10 corresponds to 0.5 second. This is a measurement response speed sufficient to use the measured flatness value in the feedback control to the finishing mill and the like. Also, in this embodiment, the threshold value M is set at 5. In order to calculate an exact degree of steepness, it is thought that measured values over a length of 5 m three times or more the width (1.65 m at the maximum) of the hot-rolled steel sheet S are necessary. Therefore, in this embodiment, the threshold value M is set at 5 so that the measurement values obtained by measuring the range of image visual view of 1 m in the longitudinal direction of the hot-rolled steel sheet S properly at least five times are outputted to the control unit.

In this embodiment, the case where the flatness is measured on the exit of the finishing mill train on the hot-rolled steel sheet production line has been described as an example. However, the present invention is not limited to this case, and can be applied to the case where the flatness is measured between the finishing mills or on the exit of the cooling zone. Hereunder, there are explained the effects achieved in the case where the flatness measuring method in accordance with this embodiment is applied.

<Concerning Picture Element Concentration Distribution>

Figure 13:
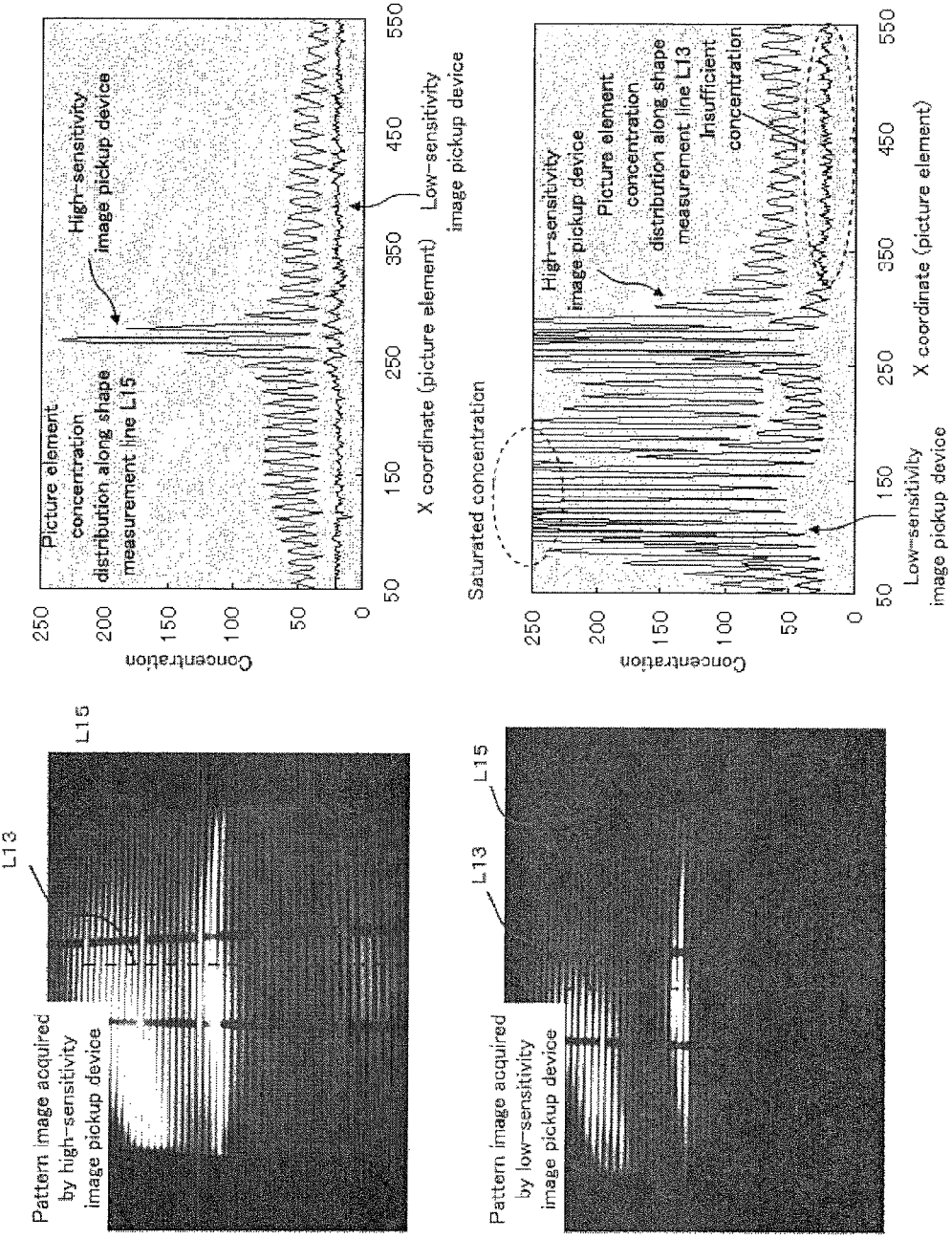
[FIG. 13]
Figure 14:
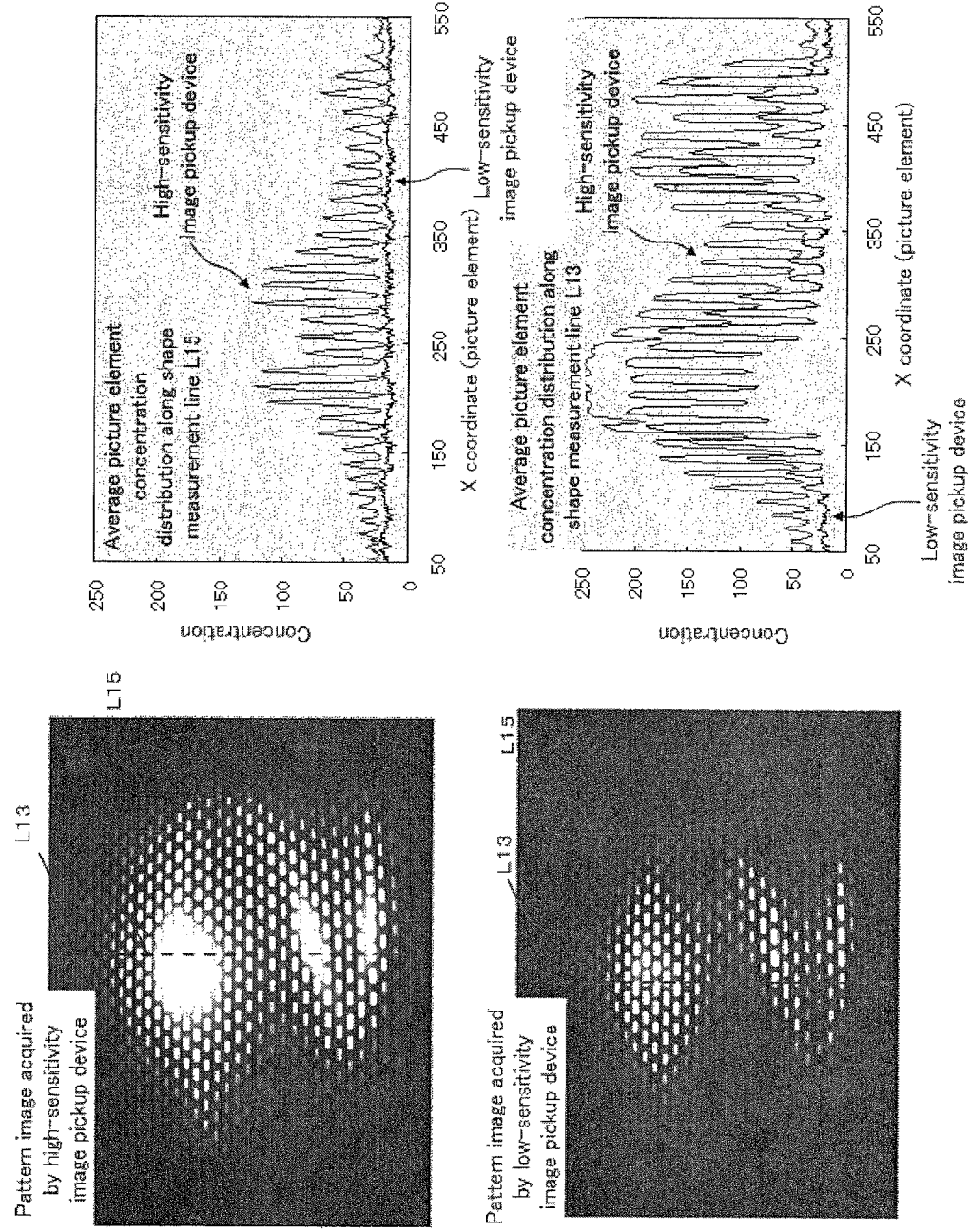
[FIG. 14]

FIG. 13 is views showing pattern image examples in the case where the conventional linear pattern is used as a light and dark pattern projected onto the surface of the hot-rolled steel sheet S and picture element concentration distributions in the pattern image along the shape measurement line L13 in the central portion in the width direction of the hot-rolled steel sheet S and along the shape measurement line L15 in the vicinity of the right-hand side edge thereof. FIG. 14 is views showing pattern image examples in the case where the staggered pattern of this embodiment is used as a light and dark pattern projected onto the surface of the hot-rolled steel sheet S and average picture element concentration distributions in the pattern image along the shape measurement line L13 in the central portion in the width direction of the hot-rolled steel sheet S and along the shape measurement line L15 in the vicinity of the right-hand side edge thereof.

The exposure time of the image pickup device at the time when the conventional linear pattern is photographed is set at 1.5 msec, whereas the exposure time thereof at the time when the staggered pattern of this embodiment is photographed is set at 2.5 msec, which is longish time, as described above because the staggered pattern is difficult to collapse even if the picture element concentration saturates. The hot-rolled steel sheets S to be measured have the same material quality and the same size, and are sheets in which poor flatness is produced in the vicinity of the front end.

As can be seen in FIGS. 13 and 14, even if either the linear pattern (FIG. 13) or the staggered pattern (FIG. 14) is used as a light and dark pattern, the influence of specularly reflected light decreases at a position farther from the central portion of the hot-rolled steel sheet S. Therefore, for the picture element concentration distribution along the shape measurement line L15 in the vicinity of the edge (in the case of FIG. 14, the average picture element concentration distribution), periodic waveform can be observed over the whole region in the longitudinal direction of pattern image by using the pattern image acquired by the high-sensitivity image pickup device.

On the other hand, in the central portion of the hot-rolled steel sheet S, in the case where the conventional linear pattern is projected, the difference in picture element concentration between the picture element region corresponding to the position at which specularly reflected light is received and other picture element regions is large. Therefore, as shown in FIG. 13, for the picture element concentration distribution along the shape measurement line L13 in the central portion in the width direction of the hot-rolled steel sheet S, periodic waveform can be observed over the whole region in the longitudinal direction of pattern image even by using the pattern image acquired by either of the high-sensitivity image pickup device and the low-sensitivity image pickup device. On the other hand, in the case where the staggered pattern of this embodiment is projected, as shown in FIG. 14, the staggered pattern is difficult to collapse even if the picture element concentration saturates, and the picture element concentrations are averaged in the width direction, so that the difference in picture element concentration between the picture element region corresponding to the position at which specularly reflected light is received and other picture element regions is small. Therefore, for the pattern image acquired by the low-sensitivity image pickup device, in the average picture element concentration distribution along the shape measurement line L13 in the central portion in the width direction of the hot-rolled steel sheet S, periodic waveform can be observed over almost the whole region in the longitudinal direction of pattern image.

<Measurement Chart of Degree of Steepness etc.>

Figure 16A:
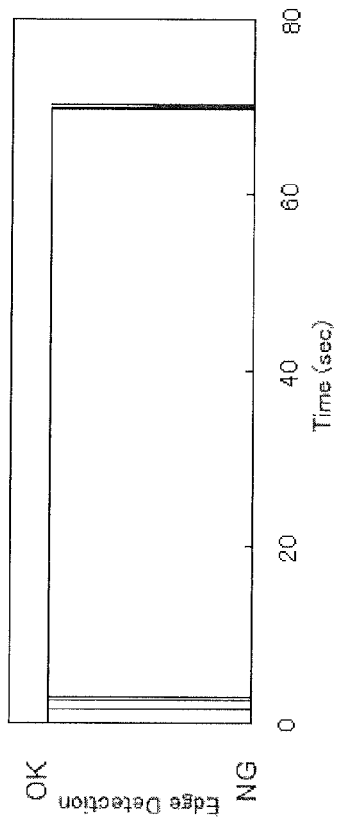
[FIG. 16]
Figure 16C:
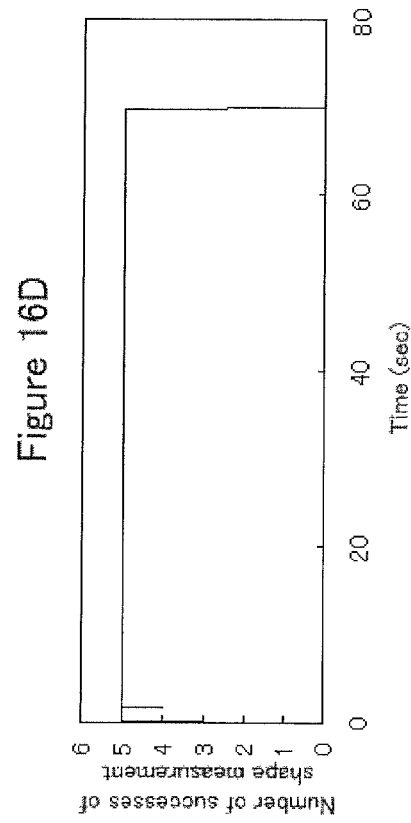
Figure 16B:
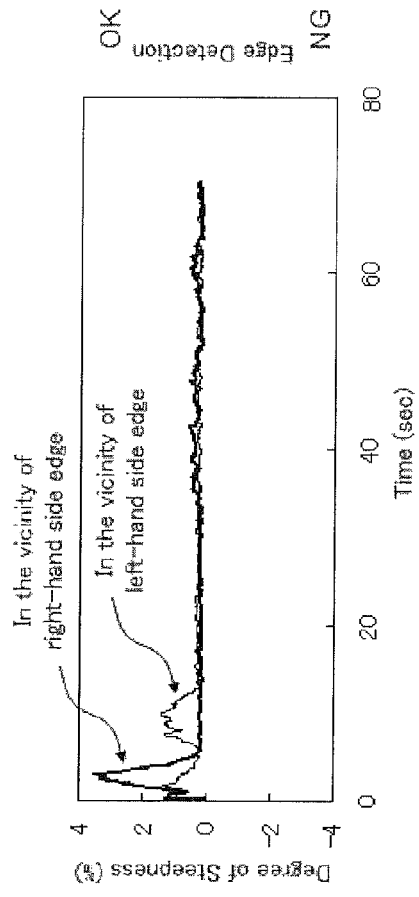
Figure 16D:
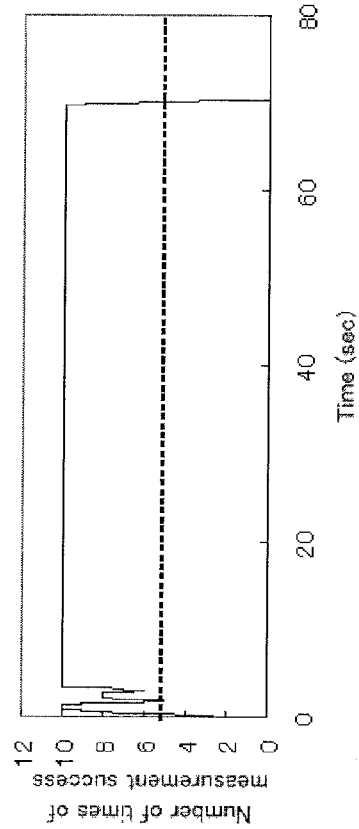

FIG. 15 shows measurement examples of degree of steepness and the like over the overall length of one coil of steel sheet in the case where the conventional linear pattern is used as a light and dark pattern projected onto the surface of the hot-rolled steel sheet S. FIG. 16 shows measurement examples of degree of steepness and the like over the overall length of one coil of steel sheet in the case where the staggered pattern of this embodiment is used as a light and dark pattern projected onto the surface of the hot-rolled steel sheet S. FIGS. 15A and 16A show the measured values of degree of steepness measured along the shape measurement lines L11 and L15 in the vicinity of both the edges, FIGS. 15B and 16B show the number of times when the measurement was successful among the measured flatness values of the latest ten times, FIGS. 15C and 16C show whether or not the edge of the hot-rolled steel sheet S could be detected, and FIGS. 15D and 16D show the number of shape measurement lines along which the surface shape could be measured properly. The hot-rolled steel sheets S to be measured have the same material quality and the same size, and are sheets in which poor flatness is produced in the vicinity of the front end.

As shown in FIG. 15, in the case where the linear pattern is used as a light and dark pattern, the edge detection is made properly over the overall length of the hot-rolled steel sheet S (FIG. 15C); however, the measurement of surface shape cannot be made properly along all of the five shape measurement lines, and in some cases, the measurement fails along some shape measurement lines. Therefore, among the measured flatness values of the latest ten times, the case occurs in which the number of times when the measurement is successful is smaller than five, so that the measured value cannot be believed, and cannot be outputted to the control unit. In particular, the front end of the hot-rolled steel sheet S, at which the flatness must inherently controlled, cannot be measured because of the non-tension state. On the other hand, as shown in FIG. 16, in the case where the staggered pattern is used as a light and dark pattern, over almost the overall length of one coil of the hot-rolled steel sheet S, not only the edge detection but also the measurement of surface shape can be made properly, which reveals that improvement has been accomplished as compared with the conventional example.

<Effect of Determination of Effectiveness>

FIG. 17 shows measurement examples of degree of steepness and the like over the overall length of one coil of steel sheet in the case where the staggered pattern of this embodiment is used as a light and dark pattern projected onto the surface of the hot-rolled steel sheet S for the hot-rolled steel sheet S having material quality of low surface reflectance. FIG. 17A shows the measured values of degree of steepness measured along the shape measurement lines L11 and L15 in the vicinity of both the edges, FIG. 17B shows the number of times when the measurement was successful among the measured flatness values of the latest ten times, FIG. 17C shows whether or not the edge of the hot-rolled steel sheet S could be detected, and FIG. 17D shows the number of shape measurement lines along which the surface shape could be measured properly.

Figure 17A:
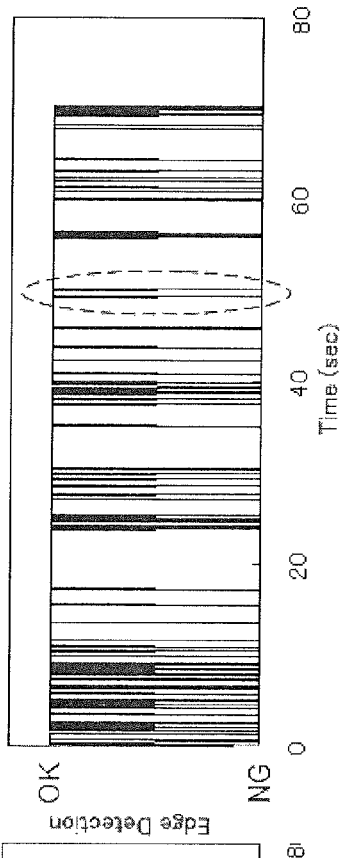
[FIG. 17]
Figure 17C:
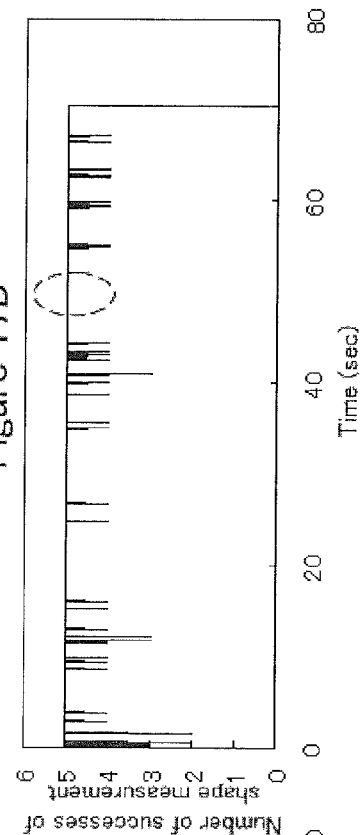
Figure 17B:
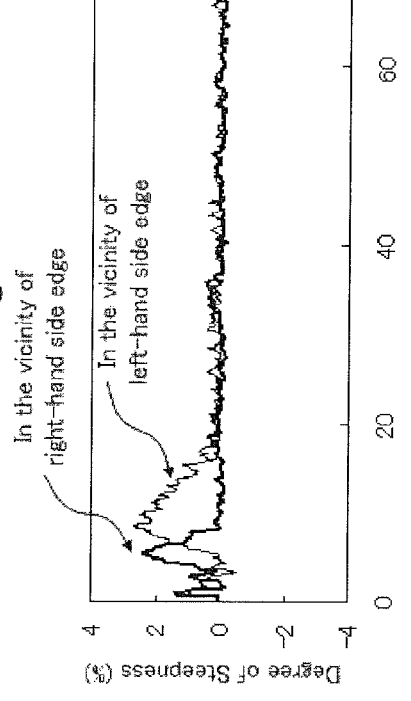
Figure 17D:
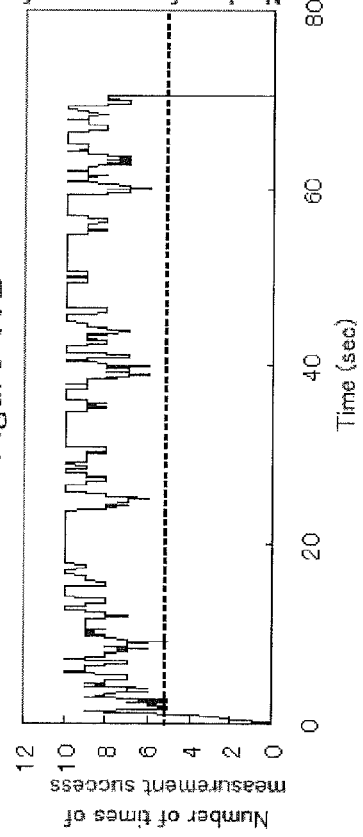

As shown in FIG. 17, in this example, the case somewhat occurs in which the edge detection cannot be made (FIG. 17C); however, if among the measured flatness values of the latest ten times, the number of times when the measurement is successful is not smaller than five, among the measured flatness values of the latest ten times, the average value of the measured flatness values succeeded in measurement is outputted to the control unit as the effective flatness measurement result, so that the flatness measurement result is outputted continuously over the overall length of one coil of the hot-rolled steel sheet S (FIG. 17B). In some cases, the surface shape could be measured properly for all of the five shape measurement lines regardless of the fact that the edge detection could not be made (locations surrounded by a broken line in FIGS. 17C and 17D). The reason for this is that in the case where it is mistakenly detected that a point on the inside of the true edge of the hot-rolled steel sheet S is the edge, the staggered pattern is projected on the inside thereof, so that the surface shape can be measured properly. This result reveals that the determination as to whether or not the measured flatness value succeeded in measurement must be made by both of, not either one of, the determinations as to whether the edge of the sheet material could be detected properly and as to whether or not the surface shape of the sheet material could be measured properly.

<Measurement Stability>

Table 1 gives one example of a result of comparison between the measurement stability in the case where the conventional linear pattern is used and the measurement stability in the case where the staggered pattern of this embodiment is used for the hot-rolled steel sheet S of the same steel type. Since the state of the surface of the hot-rolled steel sheet S differs depending on the steel type, the measurement stability is compared for a steel type that is the same as the steel type for which the surface shape measurement success percentage in the case where the conventional linear pattern is used is on the low side. The edge detection success percentage, the surface shape measurement success percentage, and the effectiveness determination percentage in Table 1 are average values of values determined by Formulas (14) to (16) for each coil of the hot-rolled steel sheet S, respectively. The method for detecting the edge and the method for measuring the surface shape are as described above.

Edge detection success percentage=(number of times when edge detection is successful/number of processed images over overall length of one coil)×100 (14)

Surface shape measurement success percentage= (number of times when surface shape measurement is successful/number of processed images over overall length of one coil)×100 (15)

Effectiveness determination percentage=(number of times when both of surface shape measurement and edge detection are successful/number of processed images over overall length of one coil)× 100 (16)

TABLE 1

| Projection pattern | Number of coils | Edge detection success percentage | Surface shape measurement success percentage | Effectiveness determination percentage |
|---|---|---|---|---|
| Linear pattern | 163 | 99.9% | 83.8% | 94.2% |
| Staggered pattern | 258 | 99.2% | 97.9% | 98.6% |

Concerning the edge detection, it can be seen that in either case, the success percentage was 99% or more, and there is scarcely a difference between the case where the linear pattern is used and the case where the staggered pattern is used. In other words, it can be said that even if the staggered pattern is used as the projection pattern, the edge detectability does not decrease. Concerning the surface shape measurement, the success percentage was 83.8% in the case where the conventional linear pattern was used, whereas the success percentage was significantly increased to 97.9% by using the staggered pattern. As the result, the effectiveness determination percentage was also increased from 94.2% to 98.6%.

As described above, considering that faulty measurement in the case where the conventional linear pattern is used occurs frequently in poor flatness portions that should be controlled inherently, it can be expected to have a great advantage when measured flatness values achieved by the use of the staggered pattern as in this embodiment are applied to the control. Moreover, by turning the control on and off based on the effectiveness determination of measurement result, mistaken control caused by an abnormal measured value can be prevented, so that steady control can be realized.

The invention claimed is:

1. A method for measuring flatness of a sheet material in which a light and dark pattern composed by a light portion and a dark portion is projected onto a surface of the sheet material running in a longitudinal direction, a pattern image is acquired by photographing the light and dark pattern by an image pickup device having an image pickup visual field larger than a width of the sheet material, and the flatness of the sheet material is measured by analyzing the acquired pattern image, comprising:

a first step of using a staggered pattern as the light and dark pattern projected onto the surface of the sheet material, the staggered pattern being composed of light portions arranged in a staggered form at a predetermined preset pitch in a longitudinal direction and a transverse direction, and projecting the staggered pattern onto the surface of the sheet material so that the longitudinal direction of the staggered pattern corresponds to the longitudinal direction of the sheet material and the transverse direction of the staggered pattern corresponds to the width direction of the sheet material;

a second step of arranging the image pickup device at a position at which the specularly reflected light on the surface of the sheet material of the staggered pattern can be received, and acquiring the pattern image by photographing the staggered pattern by the image pickup device;

a third step of setting a shape measurement line extending along the longitudinal direction of the staggered pattern at a predetermined position in the acquired pattern image;

a fourth step of averaging picture element concentrations on a straight line which passes through a picture element on the shape measurement line and extends in the transverse direction of the staggered pattern, and has a length two times or more the transverse preset pitch between the light portions to calculate an average picture element concentration;

a fifth step of calculating distribution of the average picture element concentrations along the shape measurement line; and a sixth step of calculating a surface shape of the sheet material along the shape measurement line based on the calculated average picture element concentration distribution, and calculating the flatness of the sheet material based on the calculated surface shape; wherein the method further comprises a step of, for a reference material which is placed in parallel with the running direction of the sheet material, on which flatness is measured, and has a flat surface shape, executing the first to fifth steps to calculate the average picture element concentration distribution along the shape measurement line in the pattern image acquired for the reference material, and based on the average picture element concentration distribution, calculating in advance the distribution $p_s(x)$ of longitudinal pitches between light portions of the staggered pattern along the shape measurement line in the pattern image acquired for the reference material; and the sixth step comprises:

a step of, based on the average picture element concentration distribution calculated for the sheet material, calculating the distribution $p_m(x)$ of longitudinal pitches between light portions of the staggered pattern along the shape measurement line in the pattern image acquired for the sheet material, and a step of calculating the distribution θ(x) of the inclination angles of the surface of the sheet material along the shape measurement line based on Formula (1), and calculating the surface shape of the sheet material based on the distribution θ(x) of inclination angles of the surface of the sheet material:

$$\theta(x) = \tan^{-1}\left\{\frac{(p_m(x)/p_S(x)) - 1}{\tan\alpha + (p_m(x)/p_S(x))\tan\beta}\right\} \quad (1)$$

in Formula (1), x denotes a position along the longitudinal direction of the staggered pattern in the pattern image (a position along the longitudinal direction of the sheet material), θ(x) denotes the distribution of inclination angles between the sheet material running direction and the surface of sheet material, α denotes the angle between the direction perpendicular to the sheet material running direction and the image pickup direction of image pickup device, and β denotes the angle between the direction perpendicular to the sheet material running direction and the projection direction of the staggered pattern.

2. The method for measuring flatness of a sheet material according to claim 1, wherein the third step comprises:
a step of setting an edge detection line extending in the transverse direction of the staggered pattern at a predetermined position in the acquired pattern image;
a step of calculating, successively along the edge detection line, standard deviations of picture element concentrations on a straight line which passes through the picture element on the edge detection line and extends along the longitudinal direction of the staggered pattern, and has a length two times or more the longitudinal preset pitch between light portions;
a step of, based on the magnitude of the calculated picture element concentration standard deviation, detecting the picture element corresponding to the edge of the sheet material on the edge detection line; and
a step of setting the shape measurement line with the detected picture element corresponding to the edge being a reference.

3. The method for measuring flatness of a sheet material according to claim 1, wherein
as the image pickup device, a high-sensitivity image pickup device and a low-sensitivity image pickup device having a sensitivity lower than that of the high-sensitivity image pickup device are used;
in the second step, the high-sensitivity image pickup device and the low-sensitivity image pickup device are arranged in parallel so that the image pickup visual fields thereof have portions overlapping with each other;
in the third step, the shape measurement line is set at the corresponding position in the pattern images acquired by the high-sensitivity image pickup device and the low-sensitivity image pickup device respectively; and
the sixth step comprises:
a step of counting the number of picture elements in which the concentration saturates, in the average picture element concentration distribution along the shape measurement line set in the pattern image acquired by the high-sensitivity image pickup device, and
a step of, if the number of concentration saturated picture elements is not smaller than a preset predefined threshold value, calculating the surface shape of the sheet material along the shape measurement line based on the average picture element concentration distribution along the shape measurement line set in the pattern image acquired by the low-sensitivity image pickup device, and if the number of concentration saturated picture elements is smaller than the preset threshold value, calculating the surface shape of the sheet material along the shape measurement line based on the average picture element concentration distribution along the shape measurement line set in the pattern image acquired by the high-sensitivity image pickup device.

4. The method for measuring flatness of a sheet material according to claim 1, wherein
the method further comprises:
a seventh step of measuring the flatness successively in a plurality of different portions in the longitudinal direction of the sheet material by repeatedly executing the first to sixth steps for the sheet material running in the longitudinal direction;
an eighth step of determining whether or not the measured flatness values of preset latest N times (N: integer of 2 or more) succeeded in measurement; and
a ninth step of, if among the measured flatness values of the latest N times, the number of times when it is determined that the measurement is successful is not smaller than a preset threshold value, generating a signal indicative of success in measurement, and outputting the average value of the measured flatness value succeeded in measurement among the measured flatness values of the latest N times as a flatness measurement result, and if among the measured flatness values of the latest N times, the number of times when it is determined that the measurement is successful is smaller than the threshold value, generating a signal indicative of failure in measurement.

5. The method for measuring flatness of a sheet material according to claim 4, wherein
the eighth step comprises:
a step of setting two edge detection lines extending in the transverse direction of the staggered pattern at different positions in the longitudinal direction of the staggered pattern in each of the pattern images used to obtain the measured flatness values of the latest N times;
a step of detecting the picture element corresponding to the edge of the sheet material on each of the edge detection lines; and
a step of, based on a coordinate of the detected picture element corresponding to the edge of the sheet material and the amplitude of the average picture element concentration distribution along the shape measurement line calculated in the fifth step, determining whether or not the measured flatness values of the latest N times succeeded in measurement.

6. A method for producing a steel sheet in which method a steel sheet is produced by rolling a slab, which is roughly rolled by a roughing mill, by using a finishing mill train, and thereafter by being cooled by a cooling zone, wherein
the flatness of the steel sheet is measured by the flatness measuring method described in claim 1, and based on the measurement result, rolling conditions of the finishing mill or cooling conditions of the cooling zone are controlled.

* * * * *